United States Patent
Fendel et al.

(10) Patent No.: US 9,611,318 B2
(45) Date of Patent: Apr. 4, 2017

(54) ANTI-PLASMODIUM PARASITE ANTIBODIES

(71) Applicant: Fraunhofer-Gesellschaft zur Foerderung der angewandten Forschung e.V, Munich (DE)

(72) Inventors: Rolf Fendel, Aachen (DE); Torsten Klockenbring, Aachen (DE); Stefan Barth, Aachen (DE); Stephanie Kapelski, Aachen (DE); Dominika Maskus, Aachen (DE); Rainer Fischer, Aachen (DE); Andreas Reimann, Aachen (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 14/418,677

(22) PCT Filed: Jul. 31, 2013

(86) PCT No.: PCT/EP2013/066086
§ 371 (c)(1),
(2) Date: Jan. 30, 2015

(87) PCT Pub. No.: WO2014/020062
PCT Pub. Date: Feb. 6, 2014

(65) Prior Publication Data
US 2015/0197562 A1 Jul. 16, 2015

Related U.S. Application Data

(60) Provisional application No. 61/679,380, filed on Aug. 3, 2012.

(30) Foreign Application Priority Data

Aug. 3, 2012 (EP) ..................... 12179315

(51) Int. Cl.
*A61K 39/40* (2006.01)
*C07K 16/00* (2006.01)
*C07K 16/20* (2006.01)

(52) U.S. Cl.
CPC ........ *C07K 16/205* (2013.01); *C07K 2317/21* (2013.01); *C07K 2317/56* (2013.01); *C07K 2317/565* (2013.01); *C07K 2317/73* (2013.01); *C07K 2317/92* (2013.01)

(58) Field of Classification Search
None
See application file for complete search history.

(56) References Cited

PUBLICATIONS

Rudikoff et al (Proc Natl Acad Sci USA 1982 vol. 79 p. 1979).*
MacCallum et al. J. Mol. Biol. (1996) 262,732-745.*
Pascalis et al. The Journal of Immunology (2002) 169, 3076-3084.*
Wu et al. J. Mol. Biol. (1999) 294, 151-162.*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Casset et al. (2003) BBRC 307, 198-205.*
Vajdos et al. (2002) 320, 415-428.*
Chen et al. J. Mol. Bio. (1999) 293, 865-881.*
Breedveld, F (The Lancet. Feb. 2000. 355: 735-740).*
PCT/EP2013/066086 International Search Report mailed Oct. 21, 2013.
Black et al. "Apical location of a novel EGF-like domain-containing protein of Plasmodium falciparum." Molecular and Biochemical Parasitology, Mar. 2003, 127(1):59-68.
Giraldo et al. "Vaccination with recombinant Plasmodium vivax MSP-10 formulated in different adjuvants induces strong immunogenicity but no protection." Vaccine, Dec. 10, 2009, 28(1):7-13, Elsevier Ltd, Germany.
Puentes et al. "Identifying Plasmodium falciparum merozoite surface protein-10 human erythrocyte specific binding regions." Biochmie, May 1, 2005, 87(5): 461-472, Masson, Paris, FR.

* cited by examiner

*Primary Examiner* — Jennifer Graser
(74) *Attorney, Agent, or Firm* — Wagenknecht IP Law Group PC

(57) ABSTRACT

The technology provided herein relates to novel human antibodies against *Plasmodium* parasites, in particular against the malaria parasite *Plasmodium falciparum*. The present disclosure pertains to antibodies against merozoite surface protein 10 (MSP10). These antibodies have high affinity e.g. to *Plasmodium falciparum* schizonts and merozoites, inhibit the reinvasion of merozoites into erythrocytes and thereby neutralize parasitic multiplication.

12 Claims, 8 Drawing Sheets

FIGURE 1

First epidermal growth factor-like domain of MSP-10 (SEQ ID NO: 13)

VNYICEYSKCGPNSRCYIVEKDKEQCRCRPNYIVDMSVNYFKCIP

FIGURE 4

Complete heavy chain (V heavy chain) variable regions (SEQ ID NO: 14) and light chain (V kappa) variable region (SEQ ID NO: 15) of huMAb-anti-MSP10.1

| | Framework 1 | CDR1 | Framework 2 | CDR2 | Framework 3 | CDR3 | Framework 4 |
|---|---|---|---|---|---|---|---|
| V heavy chain | EVQLVESGGGLVKPGGSLRLSCVVS | GFRISTSA | MSWVRQVPGKGGLEWVSD | ISHSGGSK | DYADSVKGRFTISRDTSKNTLYLQMNSLRAEDTALYYC AKSVGYEDISSYFRWDYHFS | QQYEHSPWT | WGQGTLVTVSS |
| V kappa chain | EIVLTQSPDSLSLSPGERATLSCRAS | QSLTAKY | LAWYQQKGQVPRLLIY | GSS | TRATGIPDRFSGSGSGTDFTLTISRLEPADSAVYYC | QQYEHSPWT | FGQGTKLEIK |

FIGURE 7

Complete heavy chain (V heavy chain) variable regions (SEQ ID NO: 14) and light chain (V kappa) variable region (SEQ ID NO: 19) of huMAb-anti-MSP10.2

| Framework 1 | CDR1 | Framework 2 | CDR2 | Framework 3 | CDR3 | Framework 4 |
|---|---|---|---|---|---|---|
| V heavy chain | | | | | | |
| EVQLVESGGDLVKPGGSLRLSCVVS | GFRIEFSA | MSWVRQVPGKGLEWVSD | ISESGGSK | DYADSVRGRFTISRDTSKNTLYLQMNSLGADETALYYC | AKSVGYFDTSGYIRWDYFDS | WGQGILVTVSS |
| V kappa chain | | | | | | |
| EIVLTQSPDTLSLSPGERATLSCRAS | QTVARHG | LAWYQQKPGQAPRLLIY | GAS | DRATGIPDRFSGSGSGTDFTLTVSGLEPEDFAVYYC | QQYGTPRT | FGQGTKLEIK |

SEQUENCE LISTING

```
<160> NUMBER OF SEQ ID NOS: 24

<210> SEQ ID NO 1
<211> LENGTH: 7
<212> TYPE: PRT
<213> ORGANISM: Homo sapiens

<400> SEQUENCE: 1

Gln Ala Leu Thr Ala Lys Tyr
1               5

<210> SEQ ID NO 2
<211> LENGTH: 3
<212> TYPE: PRT
<213> ORGANISM: Homo sapiens

<400> SEQUENCE: 2

Gly Ser Ser
1

<210> SEQ ID NO 3
<211> LENGTH: 9
<212> TYPE: PRT
<213> ORGANISM: Homo sapiens

<400> SEQUENCE: 3

Gln Gln Tyr Glu Asp Ser Pro Trp Thr
1               5

<210> SEQ ID NO 4
<211> LENGTH: 8
<212> TYPE: PRT
<213> ORGANISM: Homo sapiens

<400> SEQUENCE: 4

Gly Phe Arg Ile Ser Thr Ser Ala
1               5

<210> SEQ ID NO 5
<211> LENGTH: 8
<212> TYPE: PRT
<213> ORGANISM: Homo sapiens

<400> SEQUENCE: 5

Ile Ser Glu Ser Gly Gly Ser Lys
1               5

<210> SEQ ID NO 6
<211> LENGTH: 20
<212> TYPE: PRT
<213> ORGANISM: Homo sapiens
```

<400> SEQUENCE: 6

Ala Lys Ser Val Gly Tyr Phe Asp Thr Ser Gly Tyr Tyr Arg Trp Asp
1               5                   10                  15

Tyr Phe Asp Ser
            20

<210> SEQ ID NO 7
<211> LENGTH: 21
<212> TYPE: DNA
<213> ORGANISM: Homo sapiens

<400> SEQUENCE: 7
caggctctca ccgccaagta t                                    21

<210> SEQ ID NO 8
<211> LENGTH: 9
<212> TYPE: DNA
<213> ORGANISM: Homo sapiens

<400> SEQUENCE: 8 ggttcgtcc                                                  9

<210> SEQ ID NO 9
<211> LENGTH: 27
<212> TYPE: DNA
<213> ORGANISM: Homo sapiens

<400> SEQUENCE: 9
caacaatatg aagactcacc gtggaca                              27

<210> SEQ ID NO 10
<211> LENGTH: 24
<212> TYPE: DNA
<213> ORGANISM: Homo sapiens

<400> SEQUENCE: 10
ggattcagaa tttccacctc agcc                                 24

<210> SEQ ID NO 11
<211> LENGTH: 24
<212> TYPE: DNA
<213> ORGANISM: Homo sapiens

<400> SEQUENCE: 11
attagtgaga gtggaggtag taag                                 24

<210> SEQ ID NO 12
<211> LENGTH: 60
<212> TYPE: DNA
<213> ORGANISM: Homo sapiens

<400> SEQUENCE: 12
gcgaaatccg tgggctactt tgatacttct ggttattaca gatgggacta ctttgactcc    60

<210> SEQ ID NO 13
<211> LENGTH: 45
<212> TYPE: PRT
<213> ORGANISM: Plasmodium falciparum

<400> SEQUENCE: 13

Val Asn Tyr Ile Cys Glu Tyr Ser Lys Cys Gly Pro Asn Ser Arg Cys
1               5                   10                  15

```
Tyr Ile Val Glu Lys Asp Lys Glu Gln Cys Arg Cys Arg Pro Asn Tyr
             20                  25                  30

Ile Val Asp Met Ser Val Asn Tyr Phe Lys Cys Ile Pro
         35                  40                  45

<210> SEQ ID NO 14
<211> LENGTH: 127
<212> TYPE: PRT
<213> ORGANISM: Homo sapiens

<400> SEQUENCE: 14

Glu Val Gln Leu Val Glu Ser Gly Gly Asp Leu Val Lys Pro Gly Gly
1               5                   10                  15

Ser Leu Arg Leu Ser Cys Val Val Ser Gly Phe Arg Ile Ser Thr Ser
            20                  25                  30

Ala Met Ser Trp Val Arg Gln Val Pro Gly Lys Gly Leu Glu Trp Val
        35                  40                  45

Ser Asp Ile Ser Glu Ser Gly Gly Ser Lys Asp Tyr Ala Asp Ser Val
    50                  55                  60

Arg Gly Arg Phe Thr Ile Ser Arg Asp Thr Ser Lys Asn Thr Leu Tyr
65                  70                  75                  80

Leu Gln Met Asn Ser Leu Gly Ala Asp Asp Thr Ala Leu Tyr Tyr Cys
                85                  90                  95

Ala Lys Ser Val Gly Tyr Phe Asp Thr Ser Gly Tyr Tyr Arg Trp Asp
            100                 105                 110

Tyr Phe Asp Ser Trp Gly Gln Gly Thr Leu Val Thr Val Ser Ser
        115                 120                 125

<210> SEQ ID NO 15
<211> LENGTH: 108
<212> TYPE: PRT
<213> ORGANISM: Homo sapiens

<400> SEQUENCE: 15

Glu Ile Val Leu Thr Gln Ser Pro Asp Ile Leu Ser Leu Ser Pro Gly
1               5                   10                  15

Glu Arg Ala Thr Leu Ser Cys Arg Ala Ser Gln Ala Leu Thr Ala Lys
            20                  25                  30

Tyr Leu Ala Trp Tyr Gln Gln Lys Pro Gly Gln Val Pro Arg Leu Leu
        35                  40                  45

Ile Tyr Gly Ser Ser Thr Arg Ala Thr Gly Ile Pro Asp Arg Phe Arg
    50                  55                  60

Gly Ser Gly Ser Gly Thr Asp Phe Thr Leu Thr Ile Ser Arg Leu Glu
65                  70                  75                  80

Pro Ala Asp Ser Ala Val Tyr Tyr Cys Gln Gln Tyr Glu Asp Ser Pro
                85                  90                  95

Trp Thr Phe Gly Gln Gly Thr Lys Leu Glu Ile Lys
            100                 105

<210> SEQ ID NO 16
<211> LENGTH: 7
<212> TYPE: PRT
<213> ORGANISM: Artificial Sequence
<220> FEATURE:
<223> OTHER INFORMATION: CDR1 (VL)

<400> SEQUENCE: 16

Gln Thr Val Arg Arg Asn Ser
1               5
```

<210> SEQ ID NO 17
<211> LENGTH: 3
<212> TYPE: PRT
<213> ORGANISM: Artificial Sequence
<220> FEATURE:
<223> OTHER INFORMATION: CDR2 (VL)

<400> SEQUENCE: 17

Gly Ala Ser
1

<210> SEQ ID NO 18
<211> LENGTH: 9
<212> TYPE: PRT
<213> ORGANISM: Artificial Sequence
<220> FEATURE:
<223> OTHER INFORMATION: CDR3 (VL)

<400> SEQUENCE: 18

Gln Gln Tyr Gly Thr Ser Pro Arg Thr
1               5

<210> SEQ ID NO 19
<211> LENGTH: 108
<212> TYPE: PRT
<213> ORGANISM: Artificial Sequence
<220> FEATURE:
<223> OTHER INFORMATION: light chain (V kappa) variable region

<400> SEQUENCE: 19

Glu Ile Val Leu Thr Gln Ser Pro Asp Thr Leu Ser Leu Ser Pro Gly
1               5                   10                  15

Glu Thr Ala Thr Leu Ser Cys Arg Ala Ser Gln Thr Val Arg Arg Asn
            20                  25                  30

Ser Leu Ala Trp Tyr Gln Gln Lys Pro Gly Gln Ala Pro Arg Leu Leu
        35                  40                  45

Ile Tyr Gly Ala Ser Asp Arg Ala Thr Gly Ile Pro Asp Arg Phe Ser
    50                  55                  60

Gly Ser Gly Phe Gly Thr Asp Phe Thr Leu Thr Val Ser Gly Leu Glu
65                  70                  75                  80

Pro Glu Asp Phe Ala Val Tyr Tyr Cys Gln Gln Tyr Gly Thr Ser Pro
                85                  90                  95

Arg Thr Phe Gly Gln Gly Thr Lys Leu Glu Ile Lys
            100                 105

<210> SEQ ID NO 20
<211> LENGTH: 21
<212> TYPE: DNA
<213> ORGANISM: Artificial Sequence
<220> FEATURE:
<223> OTHER INFORMATION: CDR1 (VL)

<400> SEQUENCE: 20
cagactgtaa gaaggaactc c                                          21

<210> SEQ ID NO 21
<211> LENGTH: 9
<212> TYPE: DNA
<213> ORGANISM: Artificial Sequence
<220> FEATURE:
<223> OTHER INFORMATION: CDR2 (VL)

<400> SEQUENCE: 21

```
ggtgcatcc                                                                9

<210> SEQ ID NO 22
<211> LENGTH: 27
<212> TYPE: DNA
<213> ORGANISM: Artificial Sequence
<220> FEATURE:
<223> OTHER INFORMATION: CDR3 (VL)

<400> SEQUENCE: 22
cagcagtacg gtacttctcc tcggaca                                           27

<210> SEQ ID NO 23
<211> LENGTH: 23
<212> TYPE: DNA
<213> ORGANISM: Artificial Sequence
<220> FEATURE:
<223> OTHER INFORMATION: Primer PS5

<400> SEQUENCE: 23
atccttcgca agacccttcc tct                                               23

<210> SEQ ID NO 24
<211> LENGTH: 23
<212> TYPE: DNA
<213> ORGANISM: Artificial Sequence
<220> FEATURE:
<223> OTHER INFORMATION: Primer PS3

<400> SEQUENCE: 24
agagagagat agatttgtag aga                                               23
```

ANTI-PLASMODIUM PARASITE ANTIBODIES

CROSS REFERENCE TO RELATED APPLICATIONS

This is a national phase application under 35 USC §371 of international patent application serial no. PCT/EP2013/066086 filed 31 Jul. 2013, which claims priority to European patent application no. EP 12179315.2 filed 3 Aug. 2012 and U.S. provisional patent application No. US 61/679,380 filed 3 Aug. 2012; the contents of each are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with file "PCTEP2013066086_2015-01-29_SEQID" created on 29 Jan. 2015, filed on 30 Jan. 2015 and having a size of 8Kilobytes. The sequence listing contained in this ASCII formatted document forms part of the specification and is herein incorporated by reference in its entirety.

FIELD OF THE DISCLOSURE

The technology provided herein relates to novel human antibodies against *Plasmodium* parasites, in particular against the malaria parasite *Plasmodium falciparum*. The present disclosure pertains to antibodies against merozoite surface protein 10 (MSP10). These antibodies have high affinity e.g. to *Plasmodium falciparum* schizonts and merozoites, inhibit the reinvasion of merozoites into erythrocytes and thereby neutralize parasitic multiplication.

An antibody of the present disclosure can be a full-length antibody or an antigen-binding portion thereof. Furthermore, an antibody of the present disclosure or an antigen-binding portion thereof may be used as a cell-specific binding domain in a complex comprising the binding domain and an effector domain. Nucleic acid molecules encoding said antibodies and complexes, vectors, host cells containing the nucleic acids and methods for preparation and producing such antibodies; compositions and methods for using such antibodies for the treatment of malaria are also encompassed by the present disclosure.

BACKGROUND

About 3.3 billion people—half of the world's population—are at risk of malaria. Every year, this leads to about 250 million malaria cases and nearly one million deaths. Malaria is especially a serious problem in Africa, where one in every five (20%) childhood deaths is due to the effects of the disease. An African child has on average between 1.6 and 5.4 episodes of malaria fever each year.

Malarial diseases in humans are caused by five species of the *Plasmodium* parasite: *P. falciparum, P. vivax, P. ovale, P. knowlesi* and *P. malariae*. Each of these species is transmitted to the human via a female *Anopheles* mosquito that transmits *Plasmodium* parasites in the stage of sporozoites. Once the sporozoites enter the bloodstream of the human, they localize in liver cells, i.e. hepatocytes. One to two weeks later, the infected hepatocytes rupture and release mature parasites, the merozoites. These then begin the erythrocytic phase of malaria by attaching to and invading red blood cells, or erythrocytes. The invasion of the erythrocytes by the malarial parasites is the direct cause of malarial pathogenesis and pathology. The fever, anemia, circulatory changes, and immunopathologic phenomena characteristic of malaria are largely the result of red cell rupture and the host's immune response to parasitized erythrocytes. For these reasons, the erythrocytic stage of the *Plasmodium* life cycle is of vital importance to passive or active vaccine development and treatment of malaria.

Malaria caused by *Plasmodium falciparum* (also called malignant malaria, *falciparum* malaria or malaria tropica) is the most dangerous form of malaria, with the highest rates of complications and mortality. Almost all malarial deaths are caused by *P. falciparum*.

Resistance of *Plasmodium falciparum* to the existing anti-malarial drug chloroquine emerged in the sixties and has spread worldwide since then. In addition, the malaria parasite has developed resistance to most other anti-malarial drugs over the past decade. This poses a major threat to public health. There is every reason to believe that the prevalence and degree of anti-malarial drug resistance will continue to increase. Furthermore, many anti-malaria drugs have been notorious for their toxic side effects, e. g. mefloquin. Today, the recommended treatments against *Plasmodium falciparum* malaria are artemisinin-based combination therapies. But also against this therapy, resistances start to occur in different parts of the world, e.g. Kenya and Cambodia.[1,2]

In principle, antibodies against *Plasmodium falciparum* with appropriate specificity and activity are desirable as an anti-malaria drug. Human antibodies would be advantageous over non-human antibodies and humanized, chimeric antibodies for use in human therapy for several reasons: A human antibody is less likely to induce an immunological response in humans than antibodies that contain non-human portions. This immune response against non-human portions rules out the possibility of repeated therapies with such antibodies. In conclusion, human antibodies can be used multiple times as a treatment regimen. Furthermore, a human antibody is less likely to be recognized as a "foreign" antibody in humans. This will result in slower elimination of the human antibody from the body than a non-human or partially human antibody. Accordingly, a human antibody can be administered at lower doses or the treatment regimen can be adopted to lower frequency than non-human or partially human antibodies.

Therefore the availability of novel human antibodies for the treatment of malaria would be highly advantageous.

SUMMARY OF THE DISCLOSURE

The present disclosure relates to novel isolated human antibodies or antigen-binding portion thereof for preventing, treating and/or the diagnosis of malaria.

In a first aspect, embodiments of the disclosure relate to isolated human antibodies, or antigen-binding portion thereof, that bind to merozoite surface protein 10 (MSP-10) of *Plasmodium* parasites, in particular to MSP-10 of *Plasmodium falciparum*.

In a second aspect, embodiments of the disclosure relate to isolated human antibodies, or antigen-binding portion thereof, that bind specific to the first epidermal growth factor-like domain of MSP-10 of *Plasmodium* parasites, in particular to the first epidermal growth factor-like domain of MSP-10 of *Plasmodium falciparum* (SEQ ID NO: 13).

In a further aspect, embodiments of this disclosure relate to isolated human antibodies, or antigen-binding portion thereof, having a light chain variable region (LCVR) and a heavy chain variable region (HCVR) and comprising at least two polypeptides having a sequence selected from SEQ ID NOs: 1, 2, 3, 4, 5 and 6, wherein the antibody inhibits the growth of Plasmodium parasites, in particular of Plasmodium falciparum.

In a further aspect, embodiments of this disclosure relate to isolated human antibodies, or antigen-binding portion thereof, having a light chain variable region (LCVR) and a heavy chain variable region (HCVR) and comprising at least two polypeptides having a sequence selected from SEQ ID NOs: 16, 17, 18, 4, 5 and 6, wherein the antibody inhibits the growth of Plasmodium parasites, in particular of Plasmodium falciparum.

Furthermore, embodiments of the present disclosure relate to isolated human antibodies, or antigen-binding portion thereof, wherein the light chain variable region (LCVR) comprises a polypeptide with the sequence shown in SEQ ID NO: 15 (shown in FIG. 4).

Furthermore, embodiments of the present disclosure relate to isolated human antibodies, or antigen-binding portion thereof, wherein the light chain variable region (LCVR) comprises a polypeptide with the sequence shown in SEQ ID NO: 19 (shown in FIG. 7).

Furthermore, embodiments of the present disclosure relate to isolated human antibodies, or antigen-binding portion thereof, wherein the heavy chain variable region (HCVR) comprises a polypeptide with the sequence shown in SEQ ID NO: 14 (shown in FIG. 4 and FIG. 7).

Furthermore, embodiments of the present disclosure relate to isolated human antibodies, or antigen-binding portion thereof, wherein the light chain variable region (LCVR) comprises a polypeptide with the sequence shown in SEQ ID NO. 15 and the heavy chain variable region (HCVR) comprises a polypeptide with the sequence shown in SEQ ID NO: 14.

Furthermore, embodiments of the present disclosure relate to isolated human antibodies, or antigen-binding portion thereof, wherein the light chain variable region (LCVR) comprises a polypeptide with the sequence shown in SEQ ID NO. 19 and the heavy chain variable region (HCVR) comprises a polypeptide with the sequence shown in SEQ ID NO: 14.

In still another aspect, embodiments of this disclosure provide nucleic acids encoding said isolated antibodies or antibody fragments thereof, as well as vectors and host cells comprising such nucleic acids.

In other aspects, this disclosure relates to compositions comprising an isolated antibody or antibody fragments thereof as described herein, wherein the compositions may be useful for, or used in therapeutically and/or diagnostic applications. In one advantageous embodiment, the composition is used as a therapeutically composition for the treatment of malaria, in particular of malaria tropica.

In a further aspect, embodiments of this disclosure relate to methods for producing the antibodies or antibody fragments thereof in a host cell by transforming the host cell with a DNA construct, advantageously including a promoter having transcriptional activity in the host cell, cultivating the transformed host cell in a suitable culture medium to allow expression of said antibodies and producing the antibodies or antibody fragments thereof. The method may also include recovering or isolating the produced antibodies or antibody fragments thereof.

In a further aspect, the disclosure relates to purified complexes comprising an antibody or an antigen-binding portion thereof according to the present disclosure as a specific binding domain and an effector domain; medicaments comprising such a complex in combination with a pharmacologically acceptable carrier or diluent and the use of such a complex for treating malaria, in particular malaria tropica.

Before the disclosure is described in detail, it is to be understood that this disclosure is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 1 shows the sequence of the first epidermal growth factor-like domain of MSP10 (SEQ ID NO: 13).

FIG. 4 shows the complete heavy and light chain variable regions of huMAb-anti-MSP10.1 with the framework regions and the complementarity determining regions highlighted. CDR regions and framework regions are shown according to the analysis of IMGTN-Quest (Heavy chain sequence: SEQ ID NO. 14; Light chain sequence SEQ ID NO. 15)

FIG. 7 shows the complete heavy and light chain variable regions of huMAb-anti-MSP10.2 with the framework regions and the complementarity determining regions highlighted. CDR regions and framework regions are shown according to the analysis of IMGT/V-Quest (Heavy chain sequence: SEQ ID NO. 19; Light chain sequence SEQ ID NO. 15)

DETAILED DESCRIPTION OF THIS DISCLOSURE

Figure 2:
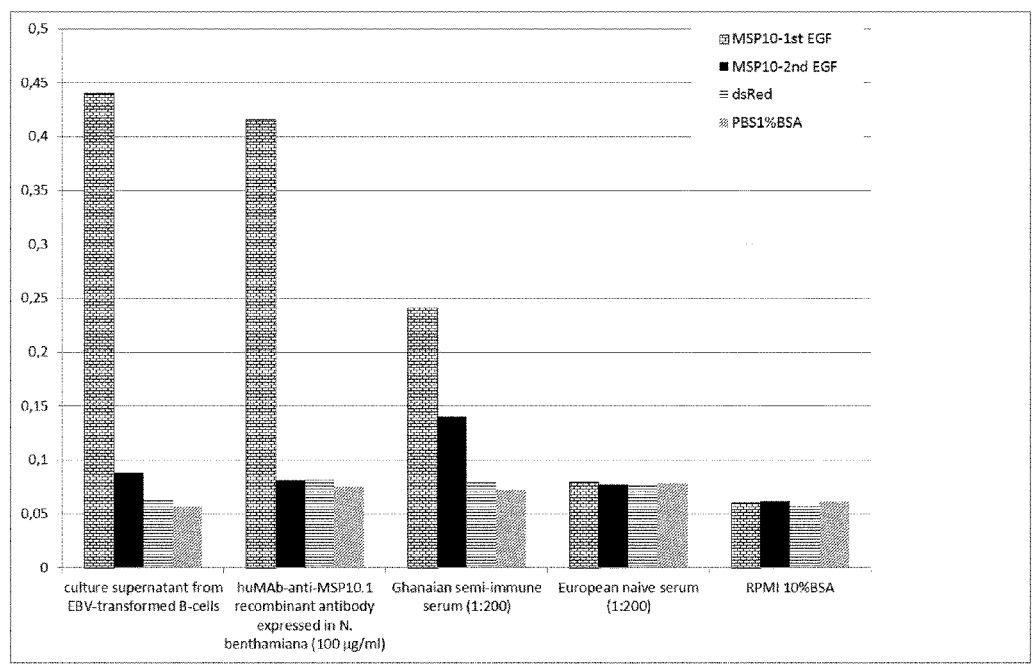
FIG. 2 is a diagram showing the results from the ELISA assay for the binding activity and specificity of the huMAb-anti-MSP10.1 antibody to the first epidermal growth factor-like domain of MSP10.

The present application discloses therapeutically and diagnostic useful isolated human antibodies, or antigen-binding portions thereof, specific for antigen-domains of the merozoite surface protein 10 (MSP10) of Plasmodium parasites, in particular of Plasmodium falciparum and characterized by high affinity binding to the parasite, and the functional capacity to inhibit the invasion of the Plasmodium parasites into the erythrocyte and/or the growth of the

*Plasmodium* parasites within the erythrocyte. These characteristics make them specifically useful as a powerful therapeutic agent.

An antibody is specific for a particular antigen if it binds that particular antigen in preference to other antigens. In particular, the antibody may not show any significant binding to molecules other than that particular antigen, and specificity may be defined by the difference in affinity between the target antigen and other non-target antigens. An antibody may also be specific for a particular epitope which may be carried by a number of antigens, in which case the antibody will be able to bind to the various antigens carrying that epitope. For example, specific binding may exist when the dissociation constant for a dimeric complex of antibody and antigen is 1 μM, preferably 100 nM and most preferably 1 nM or lower.

An antibody is an immunoglobulin molecule comprised of four polypeptide chains, two heavy (H) chains (about 50-70 kDa when full length) and two light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively.

Each heavy chain is comprised of a heavy chain variable region (abbreviated herein as HCVR) and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions[3-5]. The functional ability of the antibody to bind a particular antigen is largely determined by the CDRs.

Accordingly, in a first aspect the present disclosure provides an isolated antibody, preferably an isolated recombinant human antibody or an antigen-binding portion thereof comprising an amino acid sequence specific for the antigen MSP10 of *Plasmodium* parasites, in particular of *Plasmodium falciparum*.

In an advantageous embodiment, the antibodies of the present disclosure are specific for an epitope comprising the amino acid sequence shown in SEQ ID NO. 13. In particular, the antibodies of the present disclosure are specific for the first epidermal growth factor-like domain of MSP10 (SEQ ID NO: 13). In an advantageous embodiment, SEQ ID NO. 13 corresponds to residues 409-453 of the *Plasmodium falciparum* antigen MSP10 (Genbank entry ACR09864.1).

In a further aspect, embodiments of this disclosure relate to isolated antibodies, isolated recombinant human antibodies or antigen-binding portion thereof, having a light chain variable region (LCVR) and a heavy chain variable region (HCVR) and comprises at least two polypeptides having a sequence selected from the SEQ ID NOs: 1, 2, 3, 4, 5 and 6, listed in Table 1, wherein the antibodies inhibit the growth of *plasmodium* parasites, in particular of *Plasmodium falciparum*. The complete antibody variable regions are represented in FIG. 4. Here, the CDR regions 1, 2 and 3 from the heavy and light chain are underlined.

In a further aspect, embodiments of this disclosure relate to isolated antibodies, isolated recombinant human antibodies or antigen-binding portion thereof, having a light chain variable region (LCVR) and a heavy chain variable region (HCVR) and comprises at least two polypeptides having a sequence selected from the SEQ ID NOs: 16, 17, 18, 4, 5 and 6, listed in Table 1 and Table 2, wherein the antibodies inhibit the growth of *plasmodium* parasites, in particular of *Plasmodium falciparum*. The complete antibody variable regions are represented in FIG. 4 and FIG. 7. Here, the CDR regions 1, 2 and 3 from the heavy and light chain are underlined.

This present disclosure provides isolated human antibodies, or antigen-binding portions thereof, that bind to merozoite surface protein 10 (MSP10). Preferably, the human antibodies of the invention are recombinant, growth inhibiting human anti-MSP10 antibodies.

Table 1 shows the amino acid sequences of complementarity-determining regions 1-3 (CDR 1-3) of the antibodies' heavy and light chains.

TABLE 1

| LCVR and HCVR of MSP10-binding antibody huMAb-anti-MSP10.1 | | |
|---|---|---|
| SEQ ID # | CDR # | Amino Acid Sequence |
| SEQ ID NO: 1 | CDR1 (VL) | QALTAKY |
| SEQ ID NO: 2 | CDR2 (VL) | GSS |
| SEQ ID NO: 3 | CDR3 (VL) | QQYEDSPWT |
| SEQ ID NO: 4 | CDR1 (VH) | GFRISTSA |
| SEQ ID NO: 5 | CDR2 (VH) | ISESGGSK |
| SEQ ID NO: 6 | CDR3 (VH) | AKSVGYFDTSGYYRWDYFDS |

Table 2 shows the amino acid sequences of complementarity-determining regions 1-3 (CDR 1-3) of the light chain of huMAb-anti-MSP10.2.

TABLE 2

| LCVR of MSP10-binding antibody huMAb-anti-MSP10.2 | | |
|---|---|---|
| SEQ ID # | CDR # | Amino Acid Sequence |
| SEQ ID NO: 16 | CDR1 (VL) | QTVRRNS |
| SEQ ID NO: 17 | CDR2 (VL) | GAS |
| SEQ ID NO: 18 | CDR3 (VL) | QQYGTSPRT |

In another advantageous embodiment, the disclosure provides an isolated human antibody, preferably an isolated recombinant human antibody or antigen-binding portion thereof, comprising at least one polypeptide, preferably at least 2, 3, 4, 5 or 6 polypeptides, with a sequence selected from the group consisting of the sequences shown in CDR1 of huMAb-anti-MSP10.1 VH (SEQ ID NO: 4), CDR2 of huMAb-anti-MSP10.1 VH (SEQ ID NO: 5), CDR3 of huMAb-anti-MSP10.1 VH (SEQ ID NO: 6), CDR1 of huMAb-anti-MSP10.1 VL (SEQ ID NO: 1), CDR2 of huMAb-anti-MSP10.1 VL (SEQ ID NO: 2) or CDR3 of huMAb-anti-MSP10.1 VL (SEQ ID NO: 3), wherein said polypeptides preferably exists in said antibody at the same CDR position as shown in Table 1 herein.

In another advantageous embodiment, the disclosure provides an isolated human antibody, preferably an isolated recombinant human antibody or antigen-binding portion thereof, comprising at least one polypeptide, preferably at least 2, 3, 4, 5 or 6 polypeptides, with a sequence selected from the group consisting of the sequences shown in CDR1 of huMAb-anti-MSP10.2 VH (SEQ ID NO: 4), CDR2 of huMAb-anti-MSP10.2 VH (SEQ ID NO: 5), CDR3 of huMAb-anti-MSP10.2 VH (SEQ ID NO: 6), CDR1 of huMAb-anti-MSP10.2 VL (SEQ ID NO: 16), CDR2 of huMAb-anti-MSP10.2 VL (SEQ ID NO: 17) or CDR3 of huMAb-anti-MSP10.2 VL (SEQ ID NO: 18), wherein said polypeptides preferably exists in said antibody at the same CDR position as shown in Table 1 and Table 2 herein.

In some embodiments the LCVR comprises a polypeptide with the sequence shown in: CDR1 of huMAb-anti-MSP10.1 VL (SEQ ID NO: 1), CDR2 of huMAb-anti-MSP10.1 VL (SEQ ID NO: 2) or CDR3 of huMAb-anti-MSP10.1 VL (SEQ ID NO: 3). In another embodiment, the disclosure provides a human antibody, or antigen-binding portion thereof, comprising a LCVR comprising a polypeptide with the sequence shown in: CDR1 of huMAb-anti-MSP10.1 VL (SEQ ID NO: 1), CDR2 of huMAb-anti-MSP10.1 VL (SEQ ID NO: 2) or CDR3 of huMAb-anti-MSP10.1 VL (SEQ ID NO: 3), and further comprising a HCVR comprising a polypeptide with the sequence shown in CDR1 of huMAb-anti-MSP10.1 VH (SEQ ID NO: 4), CDR2 of huMAb-anti-MSP10.1 VH (SEQ ID NO: 5), CDR3 of huMAb-anti-MSP10.1 VH (SEQ ID NO: 6).

In some embodiments the LCVR comprises a polypeptide with the sequence shown in: CDR1 of huMAb-anti-MSP10.2 VL (SEQ ID NO: 16), CDR2 of huMAb-anti-MSP10.2 VL (SEQ ID NO: 17) or CDR3 of huMAb-anti-MSP10.2 VL (SEQ ID NO: 18). In another embodiment, the disclosure provides a human antibody, or antigen-binding portion thereof, comprising a LCVR comprising a polypeptide with the sequence shown in: CDR1 of huMAb-anti-MSP10.2 VL (SEQ ID NO: 16), CDR2 of huMAb-anti-MSP10.2 VL (SEQ ID NO: 17) or CDR3 of huMAb-anti-MSP10.2 VL (SEQ ID NO: 18), and further comprising a HCVR comprising a polypeptide with the sequence shown in CDR1 of huMAb-anti-MSP10.2 VH (SEQ ID NO: 4), CDR2 of huMAb-anti-MSP10.2 VH (SEQ ID NO: 5), CDR3 of huMAb-anti-MSP10.2 VH (SEQ ID NO: 6).

Any light chain may be combined with any heavy chain, e. g., by light and heavy chain shuffling.[6]

According to an advantageous embodiment of the present disclosure, the LCVR CDR1 domain comprises the amino acid sequence of SEQ ID NO: 1. In another embodiment, the LCVR CDR2 domain comprises the amino acid sequence of SEQ ID NO: 2. In another embodiment, the LCVR CDR3 domain comprises the amino acid sequence of SEQ ID NO: 3.

According to another advantageous embodiment of the present disclosure, there is provided a LCVR CDR1 domain comprising the amino acid sequence of SEQ ID NO: 1 and a CDR2 domain comprising the amino acid sequence of SEQ ID NO: 2. In some embodiments the LCVR CDR1 domain comprises the amino acid sequence of SEQ ID NO: 1 and the LCVR CDR3 domain comprises the amino acid sequence of SEQ ID NO: 3. In some embodiments the LCVR CDR2 domain comprises the amino acid sequence of SEQ ID NO: 2 and the LCVR CDR3 domain comprises the amino acid sequence of SEQ ID NO: 3.

According to an advantageous embodiment of the present disclosure, the LCVR CDR1 domain comprises the amino acid sequence of SEQ ID NO: 16. In another embodiment, the LCVR CDR2 domain comprises the amino acid sequence of SEQ ID NO: 17. In another embodiment, the LCVR CDR3 domain comprises the amino acid sequence of SEQ ID NO: 18.

According to another advantageous embodiment of the present disclosure, there is provided a LCVR CDR1 domain comprising the amino acid sequence of SEQ ID NO: 16 and a CDR2 domain comprising the amino acid sequence of SEQ ID NO: 17. In some embodiments the LCVR CDR1 domain comprises the amino acid sequence of SEQ ID NO: 16 and the LCVR CDR3 domain comprises the amino acid sequence of SEQ ID NO: 18. In some embodiments the LCVR CDR2 domain comprises the amino acid sequence of SEQ ID NO: 17 and the LCVR CDR3 domain comprises the amino acid sequence of SEQ ID NO: 18.

According to an advantageous embodiment of the present disclosure, the HCVR CDR1 domain comprises the amino acid sequence of SEQ ID NO: 4. In another embodiment, the HCVR CDR2 domain comprises the amino acid sequence of SEQ ID NO: 5. In another embodiment, the HCVR CDR3 domain comprises the amino acid sequence of SEQ ID NO: 6. According to another advantageous embodiment of the present disclosure, there is provided a HCVR CDR1 domain comprising the amino acid sequence of SEQ ID NO: 4 and a CDR2 domain comprising the amino acid sequence of SEQ ID NO: 5. In some embodiments the HCVR CDR1 domain comprises the amino acid sequence of SEQ ID NO: 4 and the HCVR CDR3 domain comprises the amino acid sequence of SEQ ID NO: 6. In some embodiments the HCVR CDR2 domain comprises the amino acid sequence of SEQ ID NO: 5 and the HCVR CDR3 domain comprises the amino acid sequence of SEQ ID NO: 6.

In another embodiment the LCVR comprises a polypeptide with the sequence shown in SEQ ID NO: 1 and the HCVR comprises a polypeptide with the sequence shown in SEQ ID NO: 4, or the LCVR comprises a polypeptide with the sequence shown in SEQ ID NO: 1 and the HCVR comprises a polypeptide with the sequence shown in SEQ ID NO: 5, or the LCVR comprises a polypeptide with the sequence shown in SEQ ID NO: 1 and the HCVR comprises a polypeptide with the sequence shown in SEQ ID NO: 6, or the LCVR comprises a polypeptide with the sequence shown in SEQ ID NO: 2 and the HCVR comprises a polypeptide with the sequence shown in SEQ ID NO: 4, or the LCVR comprises a polypeptide with the sequence shown in SEQ ID NO: 2 and the HCVR comprises a polypeptide with the sequence shown in SEQ ID NO: 5, or the LCVR comprises a polypeptide with the sequence shown in SEQ ID NO: 2 and the HCVR comprises a polypeptide with the sequence shown in SEQ ID NO: 6, or the LCVR comprises a polypeptide with the sequence shown in SEQ ID NO: 3 and the HCVR comprises a polypeptide with the sequence shown in SEQ ID NO: 4, or the LCVR comprises a polypeptide with the sequence shown in SEQ ID NO: 3 and the HCVR comprises a polypeptide with the sequence shown in SEQ ID NO: 5, or the LCVR comprises a polypeptide with the sequence shown in SEQ ID NO: 3 and the HCVR comprises a polypeptide with the sequence shown in SEQ ID NO: 6.

In another embodiment the LCVR comprises a polypeptide with the sequence shown in SEQ ID NO: 16 and the HCVR comprises a polypeptide with the sequence shown in SEQ ID NO: 4, or the LCVR comprises a polypeptide with the sequence shown in SEQ ID NO: 16 and the HCVR comprises a polypeptide with the sequence shown in SEQ ID NO: 5, or the LCVR comprises a polypeptide with the sequence shown in SEQ ID NO: 16 and the HCVR comprises a polypeptide with the sequence shown in SEQ ID NO: 6, or the LCVR comprises a polypeptide with the sequence shown in SEQ ID NO: 17 and the HCVR comprises a polypeptide with the sequence shown in SEQ ID NO: 4, or the LCVR comprises a polypeptide with the sequence shown in SEQ ID NO: 17 and the HCVR comprises a polypeptide with the sequence shown in SEQ ID NO: 5, or the LCVR comprises a polypeptide with the sequence shown in SEQ ID NO: 17 and the HCVR comprises a polypeptide with the sequence shown in SEQ ID NO: 6, or the LCVR comprises a polypeptide with the sequence shown in SEQ ID NO: 18 and the HCVR comprises a polypeptide with the sequence shown in SEQ ID NO: 4, or the LCVR comprises a polypeptide with the sequence shown in SEQ ID NO: 18 and the HCVR comprises a polypeptide with the sequence shown in SEQ ID NO: 5, or the LCVR comprises a polypeptide with the sequence shown in SEQ ID NO: 18 and the HCVR comprises a polypeptide with the sequence shown in SEQ ID NO: 6.

In an advantageous embodiment, the antibody according to the present disclosure is referred herein as huMAb-anti-MSP10.1. The huMAb-anti-MSP10.1 has LCVR and HCVR comprising the polypeptides having the sequences with SEQ ID NOs 1, 2, 3, 4, 5 and 6 or variant, mutants, modified form, homologue or derivative thereof, in particular having a conservative mutation.

In an advantageous embodiment, the antibody according to the present disclosure is referred herein as huMAb-anti-MSP10.2. The huMAb-anti-MSP10.2 has LCVR and HCVR comprising the polypeptides having the sequences with SEQ ID NOs 16, 17, 18, 4, 5 and 6 or variant, mutants, modified form, homologue or derivative thereof, in particular having a conservative mutation.

Further embodiments of the present disclosure relate to isolated human antibodies, or antigen-binding portion thereof, wherein the light chain variable region (LCVR) comprises a polypeptide with the sequence shown in SEQ ID NO: 15.

Further embodiments of the present disclosure relate to isolated human antibodies, or antigen-binding portion thereof, wherein the light chain variable region (LCVR) comprises a polypeptide with the sequence shown in SEQ ID NO: 19.

Furthermore, embodiments of the present disclosure relate to isolated human antibodies, or antigen-binding portion thereof, wherein the heavy chain variable region (HCVR) comprises a polypeptide with the sequence shown in SEQ ID NO: 14.

Furthermore, embodiments of the present disclosure relate to isolated human antibodies, or antigen-binding portion thereof, wherein the light chain variable region (LCVR) comprises a polypeptide with the sequence shown in SEQ ID NO: 15 and the heavy chain variable region (HCVR) comprises a polypeptide with the sequence shown in SEQ ID NO: 14.

Furthermore, embodiments of the present disclosure relate to isolated human antibodies, or antigen-binding portion thereof, wherein the light chain variable region (LCVR) comprises a polypeptide with the sequence shown in SEQ ID NO: 19 and the heavy chain variable region (HCVR) comprises a polypeptide with the sequence shown in SEQ ID NO: 14.

The variable heavy chain regions discussed above may be combined with any suitable constant region, including the constant region of gamma 1, gamma 2, gamma 3, gamma 4, mu, alpha 1, alpha 2, delta or epsilon isotypes as well as any artificial constant region.

In an advantageous embodiment, the antibodies of the present disclosure has IgG1 heavy chain constant region. Alternatively, the antibodies of the present disclosure has IgG3 heavy chain constant region.

In addition to the complete antibody, fragments of the antibody may also have the ability to bind the appropriate antigen (such as MSP10), and are therefore also encompassed by the present disclosure.

For example, it has been shown that fragments of a whole antibody can perform the function of binding antigens. Examples of binding fragments are (i) the Fab fragment consisting of LCVR, HCVR, CL and CH1 domains; (ii) the Fd fragment consisting of the HCVR and CH1 domains; (iii) the Fv fragment consisting of the LCVR and HCVR domains of a single antibody; (iv) the dAb fragment[7], which consists of a HCVR domain; (v) isolated CDR regions; (vi) F (ab') 2 fragments, a bivalent fragment comprising two linked Fab fragments (vii) single chain Fv molecules (scFv), wherein a HCVR domain and a LCVR domain are linked by a peptide linker which allows the two domains to associate to form an antigen binding site[8,9]; (viii) bispecific single chain Fv dimers (PCT/US92/09965) and (ix) "diabodies", multivalent or multispecific fragments constructed by gene fusion (WO94/13804);[10]. Fv, scFv or diabody molecules may be stabilised by the incorporation of disulphide bridges linking the HCVR and LCVR domains[11]. Minibodies comprising a scFv joined to a CH3 domain may also be made[12].

In an advantageous embodiment, the isolated antigen binding portion is a Fab fragment. Alternatively, the isolated antigen binding portion is a F(ab')$_2$ fragment or a single chain Fv fragment.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region.

The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. According to the present disclosure, the term "antibody" includes, but is not limited to recombinant antibodies, polyclonal antibodies, synthetic antibodies, monoclonal antibodies, single chain antibodies, humanized antibodies, minibodies, dibodies, tribodies as well as antibody fragments, including antigen-binding portion of the antibodies according to the present disclosure, such as Fab', Fab, F(ab')$_2$ and single domain antibodies as mentioned above. In advantageous embodiments the term "antibody" refers to a recombinant antibody, in particular to a recombinant human antibody or an antigen-binding portion thereof. The term includes also isolated antibodies like a monoclonal antibody, e.g. produced in a hybridoma cell.

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As notified above, the term "antigen-binding portion" of an antibody (or "antibody portion") includes fragments of an antibody that retain the ability to specifically bind to an antigen (e.g., MSP10). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment[7], which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv))[8,9]. Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites[10,13]. Still further, an antibody or antigen-binding portion thereof may be part of larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule[14] and use of a cysteine residue, a marker peptide and a C-terminal polyhistidine tag to make bivalent and biotinylated scFv molecules[15]. Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

In an advantageous embodiment, the antibodies or antigen-binding portion thereof according to the present disclosure are human or humanized antibodies. In advantageous embodiments the antibodies are recombinant antibodies. In some examples the antibodies have an IgG1 heavy chain constant region. Alternatively, the antibodies according to the present disclosure are antigen-binding portions like Fab fragments, F(ab)$_2$ or single chain Fv fragments.

The term "human antibody" includes antibodies having variable and constant regions corresponding to human germline immunoglobulin sequences as described by Kabat et al.[3]. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The mutations preferably are introduced using the "selective mutagenesis approach" described herein. The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In a preferred embodiment, these replacements are within the CDR regions as described in detail below. However, the term "human antibody", as used herein, is not intended to include antibodies in which CDR sequences derived from the germline of another mammalian species, such as a mouse, have been grafted onto human framework sequences. Furthermore, the term "human antibody" as used herein, is (i) an intact antibody, (ii) a substantially intact antibody, (iii) a portion of an antibody comprising an antigen-binding site, or (iv) a portion of an antibody comprising a Fab fragment, Fab' fragment or F(ab')$_2$, having variable and constant regions encoded by nucleic acid sequence information that occurs in the human germline immunoglobulin region or in recombined and/or mutated forms thereof whether or not said antibodies are produced in human cells. The term "human antibody" also includes a human antibody engineered to take the form of a single chain FV fragment. The mutations may be processed via backmutation.

The term "backmutation" refers to a process in which some or all of the somatically mutated amino acids of a human antibody are replaced with the corresponding germline residues from a homologous germline antibody sequence. The heavy and light chain sequences of the human antibody of the invention are aligned separately with the germline sequences in the VBASE database to identify the sequences with the highest homology. Differences in the human antibody of the invention are returned to the germline sequence by mutating defined nucleotide positions encoding such different amino acid. The role of each amino acid thus identified as candidate for backmutation should be investigated for a direct or indirect role in antigen binding and any amino acid found after mutation to affect any desirable characteristic of the human antibody should not be included in the final human antibody; as an example, activity enhancing amino acids identified by the selective mutagenesis approach will not be subject to backmutation. To minimize the number of amino acids subject to backmutation those amino acid positions found to be different from the closest germline sequence but identical to the corresponding amino acid in a second germline sequence can remain, provided that the second germline sequence is identical and colinear to the sequence of the human antibody of the invention for at least 10, preferably 12 amino acids, on both sides of the amino acid in question. Backmuation may occur at any stage of antibody optimization; preferably, backmutation occurs directly before or after the selective mutagenesis approach. More preferably, backmutation occurs directly before the selective mutagenesis approach.

The phrase "recombinant human antibody" includes human antibodies that are prepared, expressed, created or isolated by recombinant means, such as antibodies expressed using a recombinant expression vector transfected into a host cell (described further in Section II, below), antibodies isolated from a recombinant, combinatorial human antibody library (described in the examples), antibodies isolated from an animal (e.g., a mouse) that is transgenic for human immunoglobulin genes[16] or antibodies prepared, expressed, created or isolated by any other means that involves splicing of human immunoglobulin gene sequences to other DNA sequences. Such recombinant human antibodies have variable and constant regions derived from human germline immunoglobulin sequences[3]. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or backmutation or both.

An "isolated antibody" includes an antibody that is substantially free of other antibodies having different antigenic specificities (e.g., an isolated antibody that specifically binds MSP10 is substantially free of antibodies that specifically binds not to MSP10). Moreover, an isolated antibody may be substantially free of other cellular material and/or chemicals.

The term "inhibit" or "inhibiting" means neutralizing, antagonizing, prohibiting, preventing, restraining, slowing, disrupting, stopping, or reversing progression or severity of that which is being inhibited, e. g., including, but not limited to cell invasion, cell division, cell growing, multiplication, an activity, a disease or condition.

In an advantageous embodiment, the antibodies according to the present disclosure, or an antigen-binding portion thereof, inhibits the invasion of *Plasmodium falciparum* parasites into human red blood cells (erythrocytes). As mentioned above, the invasion of red blood cells is a key event in the infection of a subject with the malaria parasite.

A "invasion inhibiting antibody" includes an antibody whose binding to MSP10 results in inhibition of the invasion of *Plasmodium* parasites, in particular of *Plasmodium falciparum* parasites into human red blood cells. This inhibition of the invasion of human red blood cells can be measured by one or more of several standard assays known in the art (see Example 5).

In an advantageous embodiment, the antibodies according to the present disclosure, or an antigen-binding portion thereof, further may inhibits the growth i.e. neutralizes the multiplication of *Plasmodium* parasites, in particular of *Plasmodium falciparum* parasites.

A "growth inhibiting antibody" includes an antibody whose binding to MSP10 results in inhibition of the growth of *Plasmodium* parasites, in particular of *Plasmodium falciparum* parasites.

In an advantageous embodiment, the isolated human antibodies according to the present disclosure, or antigen-binding portion thereof, inhibits the invasion of *Plasmodium* parasites, in particular of *Plasmodium falciparum* parasites into the erythrocyte and/or the growth of *Plasmodium* parasites, in particular of *Plasmodium falciparum* parasites within the erythrocyte in a range of 5% to 100%, preferably 10% to 90%, more preferably 20% to 80%, more preferably 30% to 70%, more preferably 40% to 60%.

In an advantageous embodiment, the isolated human antibodies according to the present disclosure, or antigen-binding portion thereof, inhibits the invasion of *Plasmodium* parasites, in particular of *Plasmodium falciparum* parasites into the erythrocyte and/or the growth of *Plasmodium* parasites, in particular of *Plasmodium falciparum* parasites within the erythrocyte of at least 10%, of at least 20%, of at least 30%, of at least 40%, of at least 50% and in particular of at least 60% (see table 7).

The term "epitope" as used herein refers to a region of a protein molecule to which an antibody can bind. An "immunogenic epitope" is defined as the part of a protein that elicits an antibody response when the whole protein is the immunogen, as for example described gefore by Geysen et al.[17]. An "antigen binding portion" of an antibody, as used herein, refers to a region of an antibody that interacts with or binds to an epitope to which the antibody binds when the antigen binding portion is comprised within an antibody. The antigen binding portion may exist outside the context of the full length antibody and still be considered to be an antigen binding portion of the antibody whether or not it still interacts with or binds to an epitope.

The term "modified form" or "variant" means that the antibody or an antigen-binding portion thereof has been modified but retains the same functional characteristics.

The term "fusion proteins" comprises an antibody, an antigen-binding portion or any variant thereof by covalently fusing additional amino-acid sequences at the C- and/or N-terminus. The source and composition of the additional amino-acid sequence is either natural from any living organisms or virus or unnatural. In particular, the fusion protein may be a "recombinant" polypeptide which is defined either by its method of production or its structure. In reference to its method of production, e. g., a product made by a process, the process involved uses of recombinant nucleic acid techniques. In reference to structure, recombinant polynucleotides or polypeptides contain sequences from different sources. In particular, it encompasses polypeptides made by generating a sequence comprising two or more fragments which are not naturally contiguous or operably linked to each other. Thus, for example, products made by transforming cells with any unnaturally occurring vector are encompassed.

The term "homologous polypeptide" according to the present disclosure comprises any antibody or antigen-binding portion thereof with a sequence identity of at least 70% or preferably at least 80%, 85%, 90%, 95%, 97% or 99% to the LCVRs, HCVRs or CDRs according to the present disclosure.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above described changes. Amino acid residues are abbreviated according to the following Table 3 either in one- or in three-letter code.

The phrase "contact position" includes an amino acid position of in the CDR1, CDR2 or CDR3 of the heavy chain variable region or the light chain variable region of an antibody which is occupied by an amino acid that contacts antigen in one of the twenty-six known antibody-antigen structures. If a CDR amino acid in any of the 26 known solved structures of antibody-antigen complexes contacts the antigen, then that amino acid can be considered to occupy a contact position. Contact positions have a higher probability of being occupied by an amino acid which contact antigen than noncontact positions. Preferably a contact position is a CDR position which contains an amino acid that contacts antigen in greater than 3 of the 26 structures (greater than 11.5 percent). Most preferably a contact position is a CDR position which contains an amino acid that contacts antigen in greater than 8 of the 25 structures (greater than 32 percent).

The term "hypermutation position" includes an amino acid residue that occupies position in the CDR1, CDR2 or CDR3 region of the heavy chain variable region or the light chain variable region of an antibody that is considered to have a high frequency or probability for somatic hypermutation during in vivo affinity maturation of the antibody. "High frequency or probability for somatic hypermutation" includes frequencies or probabilities of a 5 to about 40 percent chance that the residue will undergo somatic hypermutation during in vivo affinity maturation of the antibody. It should be understood that all ranges within this stated range are also intended to be part of this invention, e.g., 5 to about 30 percent, e.g., 5 to about 15 percent, e.g., 15 to about 30 percent.

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin.

The term "variant of the nucleic acid molecule" refers herein to a nucleic acid molecule which is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "modification" as used herein, refers for example to substitutions, insertions or deletions of amino acid residues at specific positions in an amino acid sequence as well as the phosphorylation, acetylation like palmitoylation, methylation, sulphation, glycosylation, lipidation like isoprenylation, farnesylation, attachment of a fatty acid moiety, glypiation and/or ubiquitinylation of specific positions on the polypeptide, or combinations thereof.

The term "modifying", as used herein, includes changing one or more amino acids in the antibodies or antigen-binding portions thereof. The change can be produced by adding, substituting or deleting an amino acid at one or more positions. The change can be produced using known techniques, such as PCR mutagenesis.

TABLE 3

Amino acid abbreviations

| Abbreviations | | Amino acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons. These sets can be described in the form of a Venn diagram[18,19]. Conservative substitutions may be made, for example, according to Table 4 below which describes a generally accepted Venn diagram grouping of amino acids.

TABLE 4

Venn diagram grouping amino acids

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN[20], National Biomedical Research Foundation, Washington, D.C., which adapts the local homology algorithm of Smith and Waterman for peptide analysis.[21]. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which was described before.[22] Software for performing BLAST analyses is publicly available through the National Center for Biotechnology Information (http://www.ncbi.nlm.nih.gov/). Likewise, computer programs for determining percent homology are also readily available.

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the physical or enzymatic properties of the enzymes as explored herein.

The term "isolated" when used in relation to a nucleic acid or protein (e. g. an antibody), refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature. Preferably, an "isolated antibody" is an antibody that is substantially free of other antibodies having different antigenic specificities.

The human antibodies or antigen-binding portion thereof according to the present disclosure can also be produced in phage display libraries[23]. The techniques of Cole, et al., and Boerner, et al., are also among those techniques available for the preparation of human monoclonal antibodies[24,25].

Recombinant human antibodies may also be subjected to in vitro mutagenesis (or, when an animal transgenic for human Ig sequences is used, in vivo somatic mutagenesis) and, thus, the amino acid sequences of the HCVR and LCVR regions of the recombinant antibodies are sequences that, while derived from those related to human germline HCVR and LCVR sequences, may not naturally exist within the human antibody germline repertoire in vivo.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell which comprises a recombinant vector of the invention may also be referred to as a "recombinant host cell". Preferably the host cell is bacterial, agrobacterial, plant or mammalian; if plant, it is preferably a *Nicotiana benthamiana* plant or BY2 cells thereof, if mammalian, it is preferably a CHO, COS, NSO or 293 cell.

A wide variety of host expression systems can be used to express an antibody of the present disclosure including prokaryotic (bacterial) and eukaryotic expression systems (such as yeast, baculoviral, plant, mammalian and other animal cells, transgenic animals, and hybridoma cells), as well as phage display expression systems. An example of a suitable bacterial expression vector is pUCI 19 (Sfi), and a suitable eukaryotic expression vector is a modified pcDNA3.1 vector with a weakened DHFR selection system. Another example for a suitable eukaryotic expression vector is a modified pMS vector carrying a zeocin resistance and an IRES site[26]. An example of the plant expression vector is the pTRAkt, which is electroporated into agrobacteria and subsequently infiltrated into tobacco plants[27]. Other antibody expression systems are also known in the art and are contemplated herein.

Furthermore, an EBV-transformed human lymphoblastoid B cell line may be used as an expression system or the antibodies or binding-portions thereof can be expressed in a cell-free protein synthesis system, for example derived from an E. coli extract.

An antibody or antigen-binding portion thereof according to the present disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell. Preferably, the recombinant antibodies are secreted into the medium in which the host cells are cultured, from which the antibodies can be recovered. Standard recombinant DNA methodologies are used to obtain antibody heavy and light chain genes, incorporate these genes into recombinant expression vectors, and introduce the vectors into host cells. Such standard recombinant DNA technologies are described before[28,29] and in U. S. Pat. No. 4,816, 397 by Boss, et al.[30]

An isolated DNA encoding a HCVR region can be converted to a full-length heavy chain gene by operably linking the HCVR-encoding DNA to another DNA molecule encoding heavy chain constant regions (CH1, CH2, and CH3). The sequences of human heavy chain constant region genes are known in the art[3]. DNA fragments encompassing these regions can be obtained by standard PCR amplification. The heavy chain constant region can be an IgGl, IgG2, IgG3, IgG4, IgA, IgE, IgM or IgD constant region and any allotypic variant thereof as described in Kabat (supra), but most preferably is an IgG4 or an IgGI constant region. Alternatively, the antigen binding portion can be a Fab fragment, a F (ab') 2 fragment, or a single chain Fv fragment (scFv). For a Fab fragment heavy chain gene, the HCVR-encoding DNA can be operably linked to another DNA molecule encoding only a heavy chain CH1 constant region.

An isolated DNA encoding a LCVR region can be converted to a full-length light chain gene (as well as a Fab light chain gene) by operably linking the LCVR-encoding DNA to another DNA molecule encoding a light chain constant region, CL. The sequences of human light chain constant region genes are known in the art.[3] DNA fragments encompassing these regions can be obtained by standard PCR amplification. The light chain constant region can be a kappa or lambda constant region.

To create a scFv gene, the HCVR- and LCVR-encoding DNA fragments are operably linked to another fragment encoding a flexible linker, e. g., encoding the amino acid sequence (Gly4-Ser) 3, such that the HCVR and LCVR sequences can be expressed as a contiguous single-chain protein, with the LCVR and HCVR regions joined by the flexible linker. Examples were published by Bird et al., Huston, et al. and McCafferty, et al.[8,9,31]

To express an antibody or antigen-binding portion thereof of the disclosure, a DNA encoding a partial or full-length light and/or heavy chain, obtained as described above, may be inserted into an expression vector such that the gene is operably linked to transcriptional and translational control sequences. In this context, the term "operably linked" means that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods. Additionally, the recombinant expression vector can encode a signal peptide that facilitates secretion of the antibody light and/or heavy chain from a host cell. The human antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

In addition to the antibody heavy and/or light chain gene (s), a recombinant expression vector of the invention carries regulatory sequences that control the expression of the antibody chain gene (s) in a host cell. The term "regulatory sequence" is intended to include promoters, enhancers and other expression control elements (e. g., polyadenylation signals), as needed, that control the transcription or translation of the antibody chain gene (s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e. g., the adenovirus major late promoter (AdMLP)) and polyoma virus.

In addition to the antibody heavy and/or light chain genes and regulatory sequences, the recombinant expression vectors of the invention may carry additional sequences, such as sequences that regulate replication of the vector in host cells (e. g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced.

Further examples for selectable marker genes include the dihydrofolate reductase (DHFR) gene (for use in DHFR-minus host cells with methotrexate selection/amplification), the neo gene (for G418 selection), and glutamine synthetase (GS) in a GS-negative cell line (such as NSO) for selection/amplification.

For expression of the light and/or heavy chains, the expression vector (s) encoding the heavy and/or light chains is transfected into a host cell by standard techniques e. g, electroporation, calcium phosphate precipitation, DEAE-dextran transfection and the like.

Although it is theoretically possible to express the antibodies or the antibody fragments of the present disclosure in either prokaryotic or eukaryotic host cells, preferably eukaryotic cells, and most preferably mammalian host cells, because such cells, are more likely to assemble and secrete a properly folded and immunologically active antibody. Preferred mammalian host cells for expressing the recombinant antibodies of the invention include Chinese Hamster Ovary (CHO cells) (including DHFR-CHO cells[32]) used with a DHFR selectable marker, e. g., as described before[33], NSO myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the host cell and/or the culture medium using standard purification methods.

Host cells can also be used to produce portions, or fragments, of intact antibodies, e. g., Fab fragments or scFv molecules. It will be understood that variations on the above procedure are within the scope of the present disclosure. For example, it may be desirable to transfect a host cell with DNA encoding either the light chain or the heavy chain (but not both) of an antibody of this disclosure.

Plant cells can also be modified to create transgenic plants that express the antibody, or an antigen-binding portion thereof, of the present disclosure.

Further aspects of the disclosure relate to: a method of expressing in a host cell a antibody or a binding-portion thereof from a nucleic acid molecule as described herein; a host cell capable of expressing a polypeptide as described herein in appropriate culture conditions for producing said polypeptide; a method of producing a fusion protein comprising culturing such a host cell under appropriate conditions, which method may further comprise isolating said fusion protein from the cell culture, and which method may further comprise admixing the isolated fusion protein with a suitable further component (which may, for example, be another protein or an excipient or carrier).

As discussed above, in accordance with the present disclosure, the polypeptides may be produced in any desirable system Vector constructs and expression systems are well known in the art and may be adapted to incorporate use of polypeptides provided herein. For example, transgenic plant production is known and generation of constructs and plant production maybe adapted according to known techniques in the art.

In view of the foregoing, another embodiment of the disclosure pertains to nucleic acids, vectors, and host cell compositions that can be used for recombinant expression of the antibodies and antibody portions of the disclosure. Preferably, the disclosure provides isolated nucleic acids that comprise a region encoding one or more CDRs of huMAb-anti-MSP10.1 and even more preferably those CDRs exist in the expressed protein (e. g. antibody or antigen binding portion thereof) at the same CDR site within the antibody structure as they exist in antibody huMAb-anti-MSP10.1 (see Table 1).

In view of the foregoing, another embodiment of the disclosure pertains to nucleic acids, vectors, and host cell compositions that can be used for recombinant expression of the antibodies and antibody portions of the disclosure. Preferably, the disclosure provides isolated nucleic acids that comprise a region encoding one or more CDRs of huMAb-anti-MSP10.2 and even more preferably those CDRs exist in the expressed protein (e. g. antibody or antigen binding portion thereof) at the same CDR site within the antibody structure as they exist in antibody huMAb-anti-MSP10.2 (see Table 1 and Table 2).

Further embodiments pertains to complexes which can be regarded as heterologous complexes comprising at least two domains, i.e., one effector domain and one binding domain.

In advantageous embodiments, the present disclosure pertains to complexes which are formed from at least one antibody of the present disclosure or an antigen-binding portion thereof as a specific binding domain and at least one effector domain, wherein the antibody or antigen-binding portion thereof has a binding activity to MSP10, in particular to the first epidermal growth factor-like domain of MSP10 (SEQ ID NO: 13) of *Plasmodium falciparum*, and the effector domain carries a cytotoxic reagent as an effector function. In particular the complex comprises a fusion protein including the binding domain and the effector domain.

In certain embodiments, the binding domain as cell targeting moieties for use in the current disclosure is recombinant antibodies or antigen-binding portion thereof according to the present disclosure. The antigen-binding portion of the antibodies according to the present disclosure may be comprised in monoclonal antibodies, single chain antibodies, humanized antibodies, minibodies, dibodies, tribodies as well as antibody fragments, such as Fab', Fab, F(ab')2 or single domain antibodies.

In some embodiments, the effector domain induces apoptosis of *Plasmodium falciparum*. Alternatively, other molecules capable of eliciting the desired effector functions or anti-parasitic effects may be coupled to the antigen-binding region of the antibodies, e. g. enzymes with anti-parasitic effects. For example, the use of such antibodies may confer target selectivity to an otherwise toxic drug or substance.

Accordingly, in a further aspect the present disclosure provides an isolated nucleic acid molecule comprising a nucleic acid sequence encoding a recombinant human antibody or an antigen-binding portion thereof. Such a nucleic acid molecule may be in the form of a recombinant and preferably replicable vector.

Such vector may be any plasmid, cosmid, or phage in double or single stranded linear or circular form which may or may not be self-transmissible or mobilizable, and which can transform prokaryotic or eukaryotic host either by integration into the cellular genome or exist extrachromosomally (e. g. autonomous replicating plasmid with an origin of replication). Any suitable host may be used, including bacteria, e. g. archaebacteria, plants, plant cell, fungi.

Generally speaking, those skilled in the art are well able to construct vectors and design protocols for recombinant gene expression. For further details see, for example, Molecular Cloning: a Laboratory Manual: 2nd edition, Sambrook et al, 1989, Cold Spring Harbor Laboratory Press (or later editions of this work) and Current Protocols in Molecular Biology, Second Edition, Ausubel et al. eds., John Wiley & Sons, 1992, which are incorporated herein by reference. Preferred vectors include the plasmids pMS and PTRAkt[26, 27].

It is preferred that the antibody is secreted to the media by the cell from which it is expressed.

Further aspects of the invention relate to: a method of expressing in a host cell an antibody or an antigen-binding portion thereof as described herein from a nucleic acid molecule described herein; a host cell capable of expressing an antibody as described herein in appropriate culture conditions for producing said antibody; a method of producing an antibody comprising culturing such a host cell under appropriate conditions, which method may further comprise isolating said antibody from the cell culture, and which method may further comprise admixing the isolated antibody with a suitable further component (which may, for example, be another antibody or an excipient or carrier).

Mammalian cells may be transfected by any suitable technique such as lipofection. Alternatively, standard calcium phosphate transfection or electroporation may be used, which is well understood by the skilled person. The recombinant antibodies produced from these expression systems and nucleic acid molecules of the disclosure are preferably provided in a substantially pure or homogeneous form.

Recombinant antibodies may be purified by any suitable method affinity chromatography followed using mAB select or Protein A sepharose. This may optionally be followed by a gel filtration step, e. g. using Superdex200.

In yet a further aspect, the disclosure relates to a nucleic acid molecule and to the use of a nucleic acid molecule selected from the group consisting of
- a) a nucleic acid molecule encoding an antibody or an antigen-binding portion thereof according to the present disclosure;
- b) a nucleic acid molecule encoding for a modified form of an antibody or an antigen-binding portion thereof according to the present disclosure, preferably in which one or more amino acid residues are conservatively substituted;
- c) a nucleic acid molecule that is a fraction, variant, homologue, derivative, or fragment of the nucleic acid molecule presented as SEQ ID NO:7, SEQ ID NO:8, SEQ ID NO:9, SEQ ID NO:10 SEQ ID NO:11 and/or SEQ ID NO:12.
- d) a nucleic acid molecule encoding fragments of the isolated antibody or antigen-binding portion thereof according to the present disclosure
- e) a nucleic acid molecule that is capable of hybridizing to any of the nucleic acid molecules of a)-d) under stringent conditions
- f) a nucleic acid molecule that is capable of hybridizing to the complement of any of the nucleic acid molecules of a)-e) under stringent conditions
- g) a nucleic acid molecule having a sequence identity of at least 80% with any of the nucleic acid molecules of a)-f) and encoding for an antibody of the present disclosure or an antigen-binding portion thereof,
- h) a nucleic acid molecule having a sequence identity of at least 85% with any of the nucleic acid molecules of a)-f) and encoding an antibody of the present disclosure or an antigen-binding portion thereof,
- i) or a complement of any of the nucleic acid molecules of a)-h).

In yet a further aspect, the disclosure relates to a nucleic acid molecule and to the use of a nucleic acid molecule selected from the group consisting of
- a) a nucleic acid molecule encoding an antibody or an antigen-binding portion thereof according to the present disclosure;
- b) a nucleic acid molecule encoding for a modified form of an antibody or an antigen-binding portion thereof according to the present disclosure, preferably in which one or more amino acid residues are conservatively substituted;
- c) a nucleic acid molecule that is a fraction, variant, homologue, derivative, or fragment of the nucleic acid molecule presented as SEQ ID NO:20, SEQ ID NO:21, SEQ ID NO:22, SEQ ID NO:10 SEQ ID NO:11 and/or SEQ ID NO:12.
- d) a nucleic acid molecule encoding fragments of the isolated antibody or antigen-binding portion thereof according to the present disclosure
- e) a nucleic acid molecule that is capable of hybridizing to any of the nucleic acid molecules of a)-d) under stringent conditions
- f) a nucleic acid molecule that is capable of hybridizing to the complement of any of the nucleic acid molecules of a)-e) under stringent conditions
- g) a nucleic acid molecule having a sequence identity of at least 80% with any of the nucleic acid molecules of a)-f) and encoding for an antibody of the present disclosure or an antigen-binding portion thereof,
- h) a nucleic acid molecule having a sequence identity of at least 85% with any of the nucleic acid molecules of a)-f) and encoding an antibody of the present disclosure or an antigen-binding portion thereof,
- i) or a complement of any of the nucleic acid molecules of a)-h).

A nucleotide or nucleic acid is considered to hybridize to one of the above nucleotides if it is capable of hybridizing under conditions of medium stringency, more preferably high stringency, even more preferably under very high stringency conditions.

The nucleic acid molecule of the present disclosure may comprise nucleotide sequences that encode for SEQ ID NO:7, SEQ ID NO:8, SEQ ID NO:9, SEQ ID NO:10 SEQ ID NO:11 and/or SEQ ID NO:12, listed in Table 5.

The nucleic acid molecule of the present disclosure may comprise nucleotide sequences that encode for SEQ ID NO:20, SEQ ID NO:21, SEQ ID NO:22, SEQ ID NO:10 SEQ ID NO:11 and/or SEQ ID NO:12, listed in Table 5 and Table 6.

Table 5 shows the nucleic acid sequences of complementarity-determining regions 1-3 (CDR 1-3) of the antibody heavy and light chains.

TABLE 5

Nucleic Acid Sequences of LCVR and HCVR of MSP10-binding antibody huMAb-anti-MSP10.1

| SEQ ID # | CDR # | Nucleic Acid Sequence |
|---|---|---|
| SEQ ID NO: 7 | CDR1 (VL) | caggctctcaccgccaagtat |
| SEQ ID NO: 8 | CDR2 (VL) | ggttcgtcc |
| SEQ ID NO: 9 | CDR3 (VL) | caacaatatgaagactcaccgtgaca |
| SEQ ID NO: 10 | CDR1 (VH) | ggattcagaatttccacctcagcc |
| SEQ ID NO: 11 | CDR2 (VH) | attagtgagagtggaggtagtaag |
| SEQ ID NO: 12 | CDR3 (VH) | gcgaaatccgtgggctactttgatacttctggttattacagatgggactactttgactcc |

Table 6 shows the nucleic acid sequences of complementarity-determining regions 1-3 (CDR 1-3) of the antibody huMAb-anti-MSP10.2 light chain.

TABLE 6

Nucleic Acid Sequences of LCVR and HCVR of MSP10-binding antibody huMAb-anti-MSP10.1

| SEQ ID # | CDR # | Nucleic Acid Sequence |
|---|---|---|
| SEQ ID NO: 20 | CDR1 (VL) | cagactgtaagaaggaactcc |
| SEQ ID NO: 21 | CDR2 (VL) | ggtgcatcc |
| SEQ ID NO: 22 | CDR3 (VL) | cagcagtacggtacttctcctcggaca |

In particular, the disclosure provides a plasmid or vector system comprising a nucleic acid sequence encoding a polypeptide as described herein or a homologue or derivative thereof.

The antibodies or the antigen-binding portion thereof as well as the complexes of the present disclosure can be used with a "pharmaceutically acceptable carrier" which includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present disclosure administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In advantageous embodiments, antibodies or the antigen-binding portion thereof as well as the complexes according to the disclosure are used for preparing a medicament for preventing or treating malaria, in particular malaria tropica.

FIG. 1 shows the sequence of first epidermal growth factor-like domain of MSP-10. The domain contains 6 cysteine residues characteristic for EGF-like domains, which form disulfide bonds within the domain. The disulfide bonds within EGF-like domains (C1-C3, C2-C4, C5-C6) is represented by continuous lines.

FIG. 2 shows the results of the ELISA assay, in particular the reactivity of the huMAb-anti-MSP10.1 antibody comprising SEQ ID NO: 1 to SEQ ID NO: 6 to the first epidermal growth factor-like domain of MSP-10 (SEQ ID NO: 13). DsRed fusion constructs of EGF-like domain one (bricks), two (black solid) of MSP-10, dsRed (horizontal lines) and PBS containing 1% BSA (cross-stripped) were coated overnight on high binding 96 well plates. Reactivities of recombinant human antibody huMAb-anti-MSP10.1, supernatant from immortalized B-cell culture EBV-huMAb-anti-MSP10.1, a European malaria naïve control pool, a positive control pool of semi-immune blood donors, and culture medium alone (R10) was quantified. The activities are quantified as absorbance at 405 nm.

Figure 3:
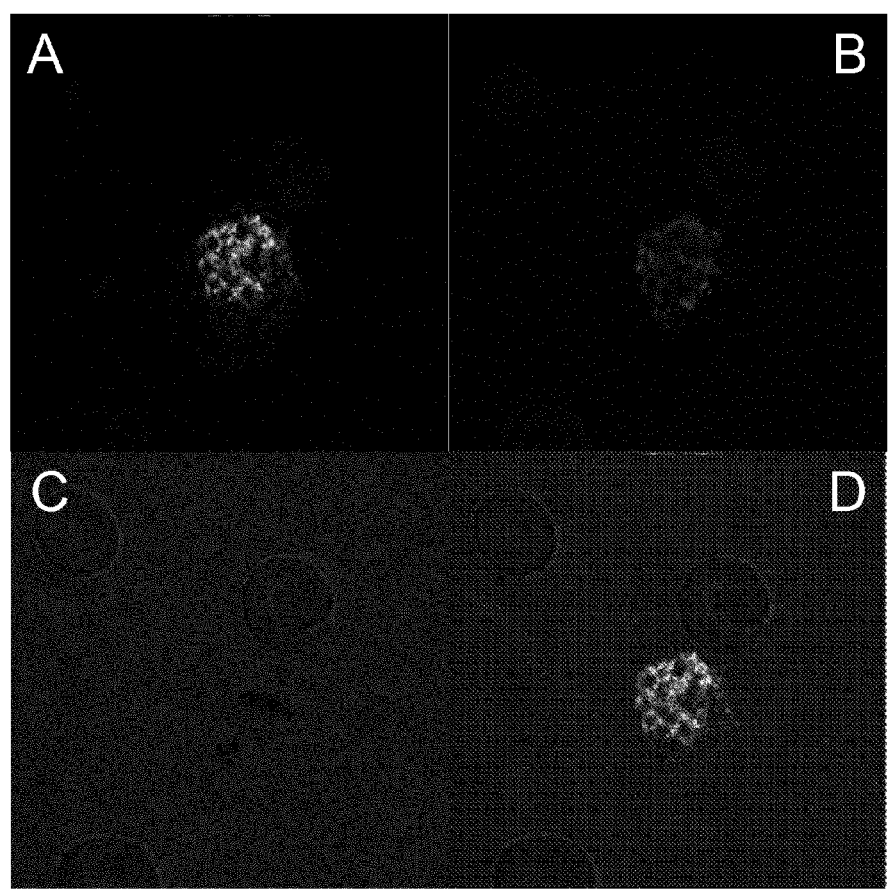
FIG. 3 shows the binding of the recombinant antibody huMAb-anti-MSP10.1 to Plasmodium falciparum schizonts by immunofluorescence assay (IFA).

FIG. 3 shows the binding of recombinant antibody huMAb-anti-MSP10.1 by immunofluorescence assay (IFA). Mature schizonts from the parasite strain 3D7 were fixed on slides and co-stained with rabbit anti-AMA1 antibody BG98 followed by a goat anti rabbit Alexa 488 (A) and recombinant human anti MSP-10 antibody huMAb-anti-MSP10.1 followed by a goat anti-human Alexa 647 (B). Panel C and D show the brightfield and the overlay of the three images. Images were taken on a Leica DM RE confocal microscope. Late stage schizonts, arrested in the very late phase using E64, display both AMA-1 antigen and MSP-10. Both antigens do not overlay together on the surface of the merozoites. Secondary antibodies alone do not show any reaction (data not shown).

FIG. 4 shows the complete heavy and light chain variable regions with the framework regions and the complementarity determining regions highlighted. Sequences were analyzed using IMGT/V-QUEST, and the Kabat definitions for framework and CDR regions were used.

Figure 5:
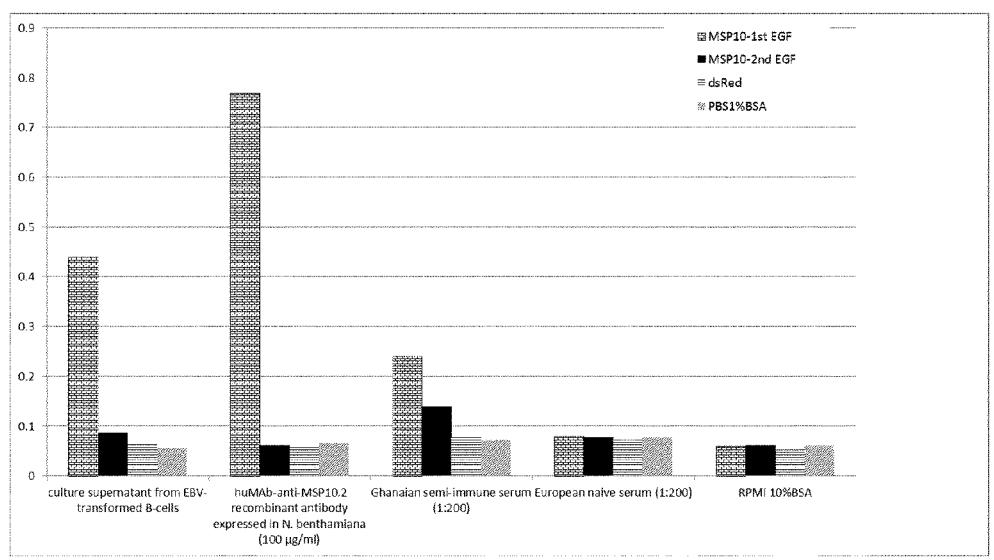
FIG. 5 is a diagram showing the results from the ELISA assay for the binding activity and specificity of the huMAb-anti-MSP10.2 antibody to the first epidermal growth factor-like domain of MSP10.

FIG. 5 shows the specific binding of huMab-anti-MSP10.2, comprising the sequences SEQ. NO. 4-6 and SEQ. NO. 16-18, to the first EGF of MSP10. Controls are the same as shown in FIG. 2.

Figure 6:
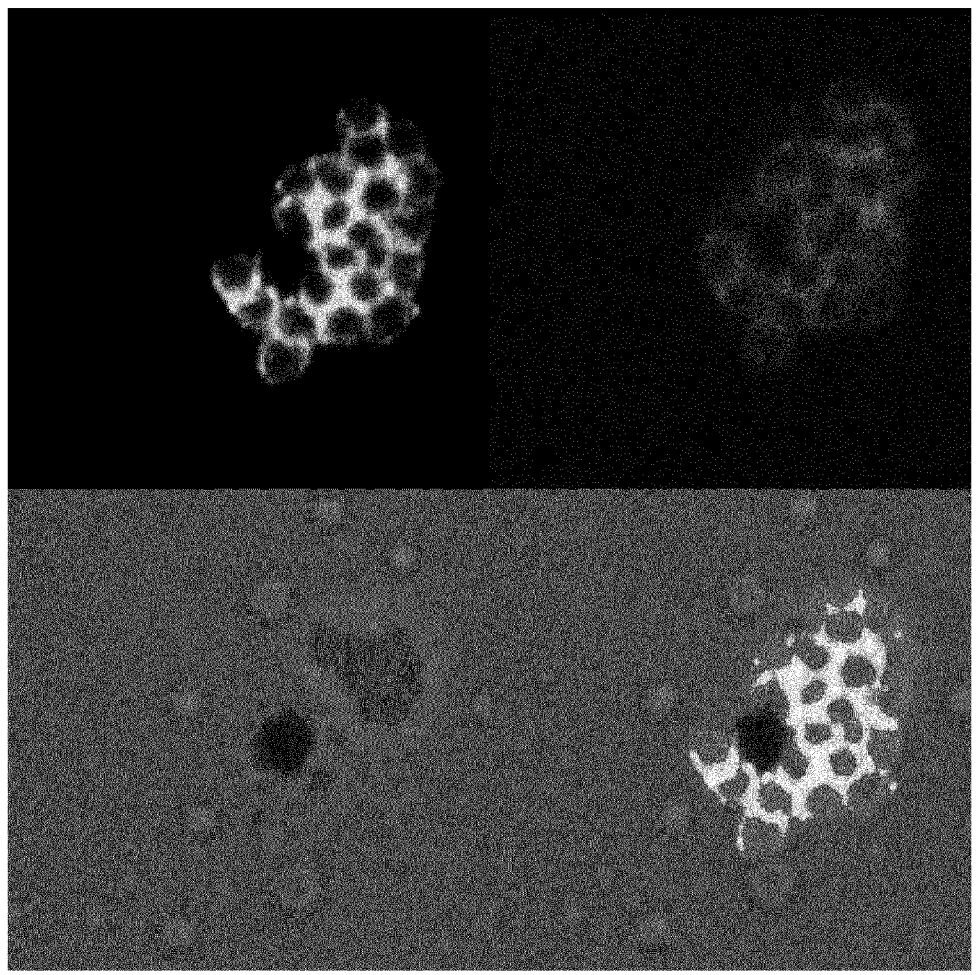
FIG. 6 shows the binding of the recombinant antibody huMAb-anti-MSP10.2 to Plasmodium falciparum schizonts by immunofluorescence assay (IFA).

FIG. 6 shows the binding of the recombinant antibody huMAb-anti-MSP10.2 by immunofluorescence assay (IFA). On a slide, mature *Plasmodium falciparum* parasites of the strain 3D7 were fixed. Subsequently, slides were co-stained with rabbit anti-AMA1 antibody BG98 followed by a goat anti-rabbit Alexa 488 (A) and recombinant human anti-MSP-10 antibody huMAb-anti-MSP10.2 followed by goat anti-human Alexa 647 (B). Panel C and D show the brightfield and the overlay of the three images. Images were taken on a Leica DM RE confocal microscope. Late stage schizonts, arrested in the very late phase using E64, display both AMA-1 antigen and MSP-10. Both antigens do not overlay together on the surface of the merozoites. Secondary antibodies alone do not show any reaction (data not shown).

FIG. 7 shows the complete heavy and light chain variable regions of the huMAb-anti-MSP10.2 with the framework regions and the complementarity determining regions highlighted. Sequences were analyzed using IMGT/V-QUEST, and the Kabat definitions for framework and CDR regions were used.

Figure 8:
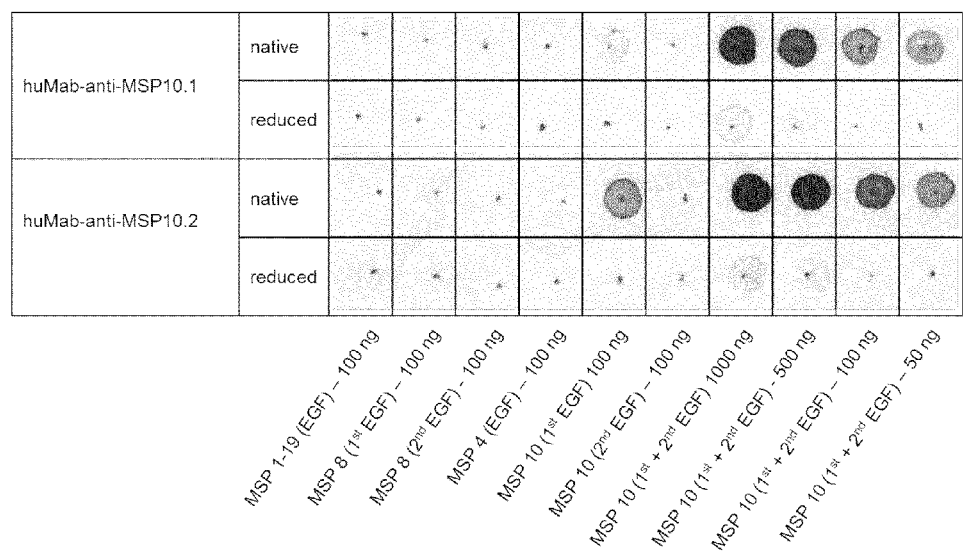
FIG. 8 shows the Dotblot of the antibodies huMAb-anti-MSP10.1 and huMAb-anti-MSP10.2 on the first EGF of MSP10 and the control proteins MSP1, MSP4, MSP8, and the second EGF of MSP10. Both native and denatured proteins are analyzed.

FIG. 8 shows the binding of the antibodies huMab-anti-MSP10.1 and huMAb-anti-MSP10.2 on conformational and not onto linear epitopes of the protein. Control proteins MSP1, MSP4 MSP8 ($1^{st}$ and $2^{nd}$ EGF) and MSP10 ($2^{nd}$ EGF) as well as the tested protein domain MSP10 ($1^{st}$ EGF) were dotted on nitrocellulose membrane and dried. After blocking, the antibodies huMab-anti-MSP10.1 and huMAb-anti-MSP10.2 were incubated on the membrane. Alkaline phosphatase coupled goat anti-human antibodies were used as secondary antibodies, before the reaction was revealed by NBT/BCIP.

The following methods and examples are offered for illustrative purposes only, and are not intended to limit the scope of the present disclosure in any way.

METHODS AND EXAMPLES

In the following examples, materials and methods of the present disclosure are provided including the determination of binding and inhibiting properties of the antibodies according to the present disclosure. It should be understood that these examples are for illustrative purpose only and are not to be construed as limiting this disclosure in any manner. All publications, patents, and patent applications cited herein are hereby incorporated by reference in their entirety for all purposes.

Example 1

Memory B Cell Immortalization and V Gene Amplification

From one Ghanaian semi-immune adult, 50 ml of blood were withdrawn and PBMCs isolated by density gradient centrifugation. PBMCs were cryopreserved in FCS containing 10% DMSO and kept at −150° C. until usage.

Memory B cells were immortalized by Epstein Barr Virus (EBV) transformation according to standard procedures[34]. Once B cell cultures were stably growing, cells were maintained in RPMI containing 10% FCS, 10 mM Hepes and 1 mM sodium pyruvate. Supernatants were collected and assayed for specificity against the antigen MSP10. Antigen-specific antibody producing cells were proliferated. Cells were grown in 75 cm² tissue culture flasks and supernatants collected. From supernatants, full length human antibodies were directly purified using IgG Sepharose 6 Fast Flow (GE lifesciences), as described in the user manual.

Using the Cells-Direct Kit (Invitrogen), cDNA was directly prepared from 10 to 100 cells. V genes were amplified from cDNA by nested PCR using primers described before[35].

Amplified sequences were cloned into the plant expression vector pTRAkt expression vector system according to standard procedures containing the heavy chain constant domain allotype IgG1m17,1 and a kappa chain constant domain for the light chain. Cloned heavy and light chain sequences were sequenced. Obtained sequences were analyzed using IMGTN-QUEST (VQUEry and Standardization) (accessible at http://www.imgt.org)[36]. The V-QUEST tool from the International Immunogenetics Information System aligns query antibody sequences to the internal antibody sequences of germline sequences. The tool also assigns the regions of the antibody corresponding to framework regions and the cluster of differentiation regions one to three. The CDR regions defining the huMAb-anti-MSP10.1 were allocated according to the results obtained from IMGT/V-QUEST.

The antibody huMAb-anti-MSP10.2 was rescued from the same EBV-transformed B-cell line. All sequencing, cloning and analysis were performed similar to huMAb-anti-MSP10.1. The CDR regions defining the huMAb-anti-MSP10.2 were allocated according to the results obtained from IMGT/V-QUEST.

From the Ghanaian donor, 1×10⁸ PBMC were recovered. The viability after thawing of the cells was 60%. During the sorting process, 8% were CD22⁺, of which 10% were IgG⁺. From these, 0.05% of cells were specific for various malaria antigens. After transformation of the B memory cells with EBV, cells were growing in clusters after 3 weeks and subcultured. Out of 90 wells which were sorted to be *P. falciparum* antigen specific, one was reacting against the first EGF-like domain of MSP10 according to the ELISA result of the tested supernatant. FIG. 1 shows the sequence of first epidermal growth factor-like domain of MSP10. The domain contains 6 cysteine residues characteristic for EGF-like domains, which form disulfide bonds within the domain. The disulfide bonds within EGF-like domains (C1-C3, C2-C4, C5-C6) is represented by continuous lines.

After V-gene rescue, IMGT/V-QUEST analysis revealed the heavy chain variable region sequence to belong to family IGHV3 (identity 87%) and the light chain variable region belong to the family IGKV3 (identity 87%). For the huMAb-anti-MSP10.2, the light chain belongs to family IGKV3 (identity 91%). Therefore, all three CDR have undergone strong affinity maturation processes in vivo. The complete variable domain from the antibody is represented in FIG. 4 and FIG. 7. The CDR regions 1-3 from both the heavy and light chains are underlined.

Example 2

Expression of Recombinant Antibodies in *Nicotiana benthamiana*

The recombinant expression of the antibodies was performed in *Nicotiana benthamiana* as described before[27]. Basically, pTRAkt vectors containing either a light chain or a heavy chain antibody sequence were electroporated into *Agrobacterium tumefaciens* strain GV3101 (pMP90RK). Successful transformation was controlled by colony-PCR using the corresponding vector primers PS5 (ATCCTTCG-CAAGACCCTTCCTCT) and PS3 (AGAGAGAGATA-GATTTGTAGAGA). Positive clones were picked and grown in YEB medium containing kanamycin (25 µg/ml) and carbenicillin (50 µg/ml) in increasing medium volume, maintaining an approximate OD of 2-4. When a volume of 1 liter was reached, agrobacteria were diluted in infiltration medium (final concentration 2 g/l glucose, 50 g/l sucrose and 0.5 g/l Ferty Mega 2, pH5.6) containing 100 µM Acetosyringon to a final OD of 1 and incubated for 1 hour. For optimal expression, agrobacteria expressing the silencing suppressor p19 were mixed at a ratio of 1:4 to the *agrobacterium* mixture. Subsequently, whole *Nicotiana benthamiana* plants were infiltrated by vacuum infiltration for 5 minutes. Infiltrated plants were kept for 5 days at room temperature in a humidified chamber. After the incubation period, whole plant protein was extracted by mixing in 2 volumes PBS in a blender for 1 minute. Plant debris was eliminated by centrifugation before antibodies were purified on a Mab-Select™ column (GE Healthcare) according to the manufactures instructions. After elution, antibodies were dialyzed against PBS and stored in aliquots at 4° C. and −20° C.

As mentioned above, the huMAb-anti-MSP10.1 antibodies were expressed in *N. benthamiana* as whole antibodies and subsequently purified. The yield of the expressed antibody typically varies between 30 and 160 mg per kg plant material. Purity and structural integrity of the antibody constructs was confirmed by SDS-PAGE under reducing and non-reducing conditions (data not shown).

The huMAb-anti-MSP10.2 was expressed and analyzed in *N. benthamiana* in a similar way as the huMAb-anti-MSP10.1.

Example 3

Determination of Antibody Specificity

Antibody specificity was estimated in a standard ELISA procedure. In short, the recombinantly produced MSP10 ($1^{st}$ EGF)-dsRed fusion, MSP10 ($2^{nd}$ EGF)-dsRed fusion and dsRed, all produced in *N. benthamiana* was coated overnight at 4° C. After a blocking step with PBS/1% BSA for 1 h at RT, the primary antibodies or human plasma was added at indicated dilutions and incubated for 1 hour at RT. After 3 washing steps using PBS/0.1% Tween20, the secondary goat anti-human IgG-alkaline phosphatase H+L specific, Promega (1:5000 in PBS) was added and also incubated for 1 hour at RT. After a final washing step (3× 1 minute in PBS/1% Tween), the binding antibodies were visualized using pNPP (Sigma, N2765). Reactivities were quantified using a Biotek Epoch Spectrophotometer at a wavelength of 405 nm.

The isolated huMAb-anti-MSP10.1 antibody presented here shows high binding specificity to the target antigen MSP10, it behaves similar to the antibody supernatant of the EBV-transformed B-cells (FIG. 1). Within MSP10, there are two EGF-like domains. The recombinant human huMAb-anti-MSP10.1 antibody does bind to the first EGF-like domain of MSP10 (SEQ ID NO.13), but not to the second one (see FIG. 2).

The other isolated antibody, huMAb-anti-MSP10.2, binds specifically to the first EGF-like domain of MSP10 (SEQ ID NO. 13), but similar to the huMAb-anti-MSP10.1, does not bind to the second one (FIG. 5).

In order to investigate whether the antibody binds a linear or a conformational epitope, Dot Blot on the native and reduced first EGF-like domain of MSP-10 was performed. As controls for unspecific staining of the huMab-anti-MSP10.1 and the huMAb-anti-MSP10.2, Dot Blot and native and reduced EGF domains of MSP-1, MSP-4 and MSP-8 were performed. For reduction process, all proteins were incubated at 56° C. with 5 mM DTT for 45 minutes. Subsequently, proteins were alkylated with freshly prepared iodoacetamide at 14 mM in order to block thiols of proteins. The reaction was quenched by addition of 5 mM DTT and incubation for 15 minutes at room temperature. Subsequently, proteins were blotted on nitrocellulose and dried for 30 minutes. The membrane was blocked using PBS/5% non-fat milk powder. Subsequently, the primary antibody was added for 1 hour in PBS/5% non-fat milk powder for 1 hour at RT. After five washing steps with PBS/0.05% Triton X-100, alkaline phosphatase conjugated goat anti-human IgG (Jackson Immunoresearch) was added at a dilution of 1:5000. After another washing step, the reaction was revealed using NBT/BCIP. The reaction of the antibody could be determined to be specific for conformational epitopes of the first EGF-like domain of MSP10 (FIG. 8). No binding of the antibodies was detected against MSP1, MSP4, MSP8 or the second EGF-like domain of MSP10. Denaturation of the MSP10 resulted in the abortion of binding activity. This demonstrates that the antibody recognizes only conformational epitopes and not only linear epitopes.

Binding assays were performed on a Biacore T200 instrument at 25° C. using a protein-A capture assay and HBS-EP as running buffer[37]. All antibodies were diluted into running buffer to yield equivalent capture levels. The injection time was set to 180 s and dissociation was recorded for 600 s. The protein-A surface was regenerated by a 60 s pulse with 30 mM HCl. For each antibody a buffer injection was used for double referencing. Values for the KD of each antibody were calculated according to the curve-fitting methodology for a simple binding model (1:1 Langmuir).

The results of the affinity measurements are summarized in Table 9.

Example 4

Immunofluorescence Microscopy

Immunofluorescence Assay (IFA) was performed as described before.[38] Plasmodium falciparum parasites were washed thrice in RPMI+25 mM Hepes, resuspended in foetal calf serum (FCS), smeared on a slide and fixed at −20° C. in 100% methanol. Using a hydrophobic slide marker pen, areas for the various antibody incubations were divided. Primary antibodies huMAb-anti-MSP10.1 and polyclonal rabbit serum BG98 specific for AMA-1 (kindly provided by Ed Remarque)[39] were incubated for 1 h at RT at a concentration of 25 µg/ml in PBS/1% FCS in a humid chamber. Subsequently, slides were washed 4× with PBS. Secondary Goat-anti human IgG-Alexa647 (Dianova, #109-605-003) and Goat-anti rabbit IgG-Alexa488 (Dianova, #111-545-003) were incubated at a dilution of 1:100 in PBS/1% FCS for 1 hour at RT. After a final washing step, slides were sealed using Vectashield Mounting Medium and subsequently analysed using a Leica DM RE confocal microscope.

The second antibody disclosed here, huMAb-anti-MSP10.2, was used in a similar way in IFA assay.

FIG. 3 shows the binding of the recombinant antibody huMAb-anti-MSP10.1 by immunofluorescence assay (IFA). Mature schizonts from the parasite strain 3D7 were fixed on slides and co-stained with rabbit anti-AMA1 antibody BG98 followed by a goat anti rabbit Alexa 488 (A) and recombinant human anti MSP10 antibody huMAb-anti-MSP10.1 followed by a goat anti-human Alexa 647 (B). Panel C and D show the brightfield and the overlay of the three images, respectively.

FIG. 6 shows the binding of the recombinant antibody huMAb-anti-MSP10.2 by immunofluorescence assay (IFA). Mature schizonts from the parasite strain 3D7 were fixed on slides and co-stained with rabbit anti-AMA1 antibody BG98 followed by a goat anti rabbit Alexa 488 (A) and recombinant human anti MSP10 antibody huMAb-anti-MSP10.2 followed by a goat anti-human Alexa 647 (B). Panel C and D show the brightfield and the overlay of the three images, respectively.

MSP10 is supposed to be localized at the polar cap (either rhoptries or micronemes) and the surface of merozoites[40]. In the immunofluorescence assay, the huMAb-anti-MSP10.1 strongly stains a region at the apical end. In addition a dim staining is detectable on the surface of merozoites. In the IFA, the huMAb-anti-MSP10.1 staining does not co-localize with anti-AMA-1 staining (see FIG. 3). No fluorescence was detected in ring stage or trophozoite stage parasites. This is in agreement with previous data from Black et al.[40].

Example 5

Growth-Inhibition Assay (GIA)

Antibodies to be tested were purified using Protein A columns. The eluate was filter sterilized. Subsequently, the antibodies were concentrated and the buffer exchanged to RPMI containing 25% Hepes. The concentrations were estimated by Bradford Assay against an antibody standard.

The growth inhibitory potential against plasmodium parasites was performed using a standardized protocol. The Plasmodium falciparum parasite strain 3D7A (provided by MR4) was maintained in culture at parasitemias below 5% at a haematocrit of 4% in RPMI medium supplemented with 10% Albumax II (Invitrogen), 25 mM Hepes, 12 µg/ml gentamicin and 100 µM hypoxanthine at 37° C. and 5% $CO_2$, 5% $O_2$ and 90% $N_2$. The cultures were maintained in a daily routine and parasitemia estimated by Giemsa staining. The erythrocytes used in the assay were mixed from 15 malaria-naïve blood donors and not older than 3 weeks. The erythrocytes were stored in SAG-Mannitol at 4° C. The parasites were synchronized by 10% Sorbitol treatment within a time window of 1-16 hours post invasion. For the assay, only highly synchronous cultures 36 to 40 hours post invasion were used.

Parasites and fresh RBCs and antibodies were mixed in a 96-well plate appropriately in order to have a final parasitemia of 0.1% and a final hematocrit of 2%. For the background control, only RBCs without parasites were kept in culture under the same conditions as the parasites. A growth control for the monitoring the parasite growth was performed by culturing the *Plasmodium falciparum* parasite without additions. All samples were measured in triplicates. As negative control, malaria-naïve rabbit and human plasma were derived purified antibodies were tested. For positive control of complete invasion inhibition, EDTA (4 mM final concentration) and BG98 rabbit anti-AMA-1 polyclonal antibodies were used. Antibodies to be tested were purified antibodies from EBV supernatants and recombinant huMAb-anti-MSP10.1.

Furthermore, the recombinant huMAb-anti-MSP10.2 was tested.

The plates were incubated at 37° C., 95% humidity, 5% $CO_2$, 5% $O_2$, and 90% $N_2$ for 40 to 44 hours. At harvest, wells were washed once with cold PBS and frozen down. Parasite growth was estimated by a Malstat™ assay[41]. Absorbance was measured after 30 minutes at a wavelength of 655 nm using a spectrophotometer. Inhibitory capacity was estimated by the following formula:

$$\% \text{ inhibition} = 100\% - \frac{(A655\ IgG\ \text{sample} - A655\ RBC\ \text{control})}{(A655\ \text{Schizont control} - A655\ RBC\ \text{control})} * 100\%$$

In order to test the inhibitory capacity of the huMAb-anti-MSP10.1, the above mentioned growth inhibition assay with the huMAb-anti-MSP10.1 was performed. The recombinant antibody efficiently inhibits the growth of *Plasmodium falciparum* to superior of 60% (Table 7). This value is similar to purified human plasma and purified antibody from transformed B-cells. The results from the standardized samples confirm the reproducibility of the assay in comparison with the European Malaria Reference Repository. The antibody BG98 inhibits the invasion and growth of the malaria parasite by 85-100%. The negative controls (IgG purified from malaria naïve blood donors did not show any inhibitory effect (Table 7).

In order to test the inhibitory capacity of the huMAb-anti-MSP10.2, the above mentioned growth inhibition assay with the huMAb-anti-MSP10.2 was performed. The recombinant antibody efficiently inhibits the growth of *Plasmodium falciparum* to superior of 70% (Table 8). This value is slightly superior to purified human plasma and purified antibody from transformed B-cells (Table 7).

The results from the standardized samples confirm the reproducibility of the assay in comparison with the European Malaria Reference Repository. The antibody BG98 inhibits the invasion and growth of the malaria parasite by 85-100%. The negative controls (recombinant IgG against an antibody against gp120 of HIV (clone 2G12)) did not show any inhibitory effect (Table 8).

TABLE 7

Growth Inhibition of the huMAb-anti-MSP10.1 on *Plasmodium falciparum* parasites

| Antibody | Inhibition (StDev) |
| --- | --- |
| purified IgG from huMAb-anti-MSP10.1 culture supernatant (0.5 mg/ml) | 58.83 (6.5) |
| recombinant huMAb-anti-MSP10.1 (2.5 mg/ml) | 61.42 (6.8) |
| BG98 positive control (6 mg/ml) | 97.74 (0.71) |
| purified antibody from naive human serum (6 mg/ml) | 1.61 (1.6) |
| purified antibody from semi immune blood donor (6 mg/ml) | 62.5 (3.4) |

TABLE 8

Growth Inhibition of the huMAb-anti-MSP10.1 on *Plasmodium falciparum* parasites

| Antibody | Inhibition (StDev) |
| --- | --- |
| recombinant huMAb-anti-MSP10.2 (2.5 mg/ml) | 70.24 (2.0) |
| BG98 positive control (6 mg/ml) | 94.40 (0.36) |
| Anti-HIV (gp120 (clone 2G12) (6 mg/ml) | 3.37 (2.2) |

This data confirms the specificity of the huMAb-anti-MSP10.1 and huMAb-antiMSP10.2. This is the first time that a human recombinant antibody against MSP10 is presented. It is also shown the first time, that an antibody specific for MSP10 can efficiently inhibit the parasite growth. This confirms the potential of this antibody to be used as a therapeutic or preventive passive vaccine.

TABLE 9

Affinity of the huMAb-anti-MSP10.1 and huMAb-anti-MSP10.1 on soluble *Plasmodium falciparum* MSP10 EGF-like domain 1

| Antibody | KD value |
| --- | --- |
| recombinant huMAb-anti-MSP10.1 | $1 \times 10^{-6}$ |
| recombinant huMAb-anti-MSP10.2 | $5.46 \times 10^{-9}$ |
| purified IgG from huMAb-anti-MSP10.1 culture supernatant | $6.29 \times 10^{-9}$ |

Advantageous Embodiments of the Present Disclosure Pertain to:
  isolated human antibodies, or antigen-binding portions thereof, that binds to merozoite surface protein 10 (MSP-10) of *Plasmodium* parasites, in particular to MSP-10 of *Plasmodium falciparum*.
  isolated human antibodies, or antigen-binding portions thereof, that binds specific to the first epidermal growth factor-like domain of MSP-10 of *Plasmodium* parasites, in particular to the first epidermal growth factor-like domain of MSP-10 of *Plasmodium falciparum* (SEQ ID NO: 13), wherein
  the isolated antibodies or antigen-binding portions thereof may inhibit the invasion of the *Plasmodium* parasite into the erythrocyte and/or the growth of the *Plasmodium* parasite within the erythrocyte.
  the isolated antibodies or antigen-binding portions thereof may inhibit the invasion of *Plasmodium* parasite into the erythrocyte and/or the growth of *Plasmodium* parasite within the erythrocyte in a range of 5% to 100%, preferably 10% to 90%, more preferably 20% to 80%, more preferably 30% to 70%, more preferably 40% to 60%.
  the isolated antibodies or antigen-binding portions thereof may inhibit the invasion of a *Plasmodium* parasite into the erythrocyte and/or the growth of a *Plasmodium* parasite within the erythrocyte of at least 10%, of at least 20%, of at least 30%, of at least 40%, of at least 50% and in particular of at least 60%.
  the isolated antibodies or antigen-binding portions thereof may be antibodies from human B-cell cultures, recombinant antibodies, synthetic antibodies or antigen-binding portions thereof.
  the isolated antibodies or antigen-binding portions thereof may have a light chain variable region (LCVR) and a heavy chain variable region (HCVR) and comprise at least two polypeptides having a sequence selected from SEQ ID NOs 1, 2, 3, 4, 5 and 6, or homologous polypeptides thereof.

the isolated antibodies or antigen-binding portions thereof may have a light chain variable region (LCVR) and a heavy chain variable region (HCVR) and comprise at least two polypeptides having a sequence selected from SEQ ID NOs 16, 17, 18, 4, 5 and 6, or homologous polypeptides thereof.

In some embodiments, the isolated human antibody or the antigen-binding portion thereof according to the present disclosure has the following characteristics:
a) inhibits the invasion or growth of *Plasmodium* parasites;
b) has a LCVR CDR1 comprising the amino acid sequence of SEQ ID NO: 1; and
c) has a HCVR CDR3 comprising the amino acid sequence of SEQ ID NO: 6, and
   may further has a LCVR CDR2 comprising the amino acid sequence of SEQ ID NO: 2, and a HCVR CDR2 comprising the amino acid sequence of SEQ ID NO: 5, and/or
   may further has a LCVR CDR3 comprising the amino acid sequence of SEQ ID NO: 3, and a HCVR CDR1 comprising the amino acid sequence of SEQ ID NO: 4.
or
a) inhibits the invasion and/or growth of *Plasmodium* parasites;
b) has a LCVR CDR1 comprising the amino acid sequence of SEQ ID NO: 1; and
c) has a HCVR CDR2 comprising the amino acid sequence of SEQ ID NO: 5, and
   may further has a LCVR CDR2 comprising the amino acid sequence of SEQ ID NO: 2, and a HCVR CDR1 comprising the amino acid sequence of SEQ ID NO: 4, and/or
   may further has a LCVR CDR3 comprising the amino acid sequence of SEQ ID NO: 3, and a HCVR CDR3 comprising the amino acid sequence of SEQ ID NO: 6.
or
a) inhibits the invasion and/or growth of *Plasmodium* parasites;
b) has a LCVR CDR1 comprising the amino acid sequence of SEQ ID NO: 1; and
c) has a HCVR CDR1 comprising the amino acid sequence of SEQ ID NO: 4, and
   may further has a LCVR CDR2 comprising the amino acid sequence of SEQ ID NO: 2, and a HCVR CDR2 comprising the amino acid sequence of SEQ ID NO: 5, and/or
   may further has a LCVR CDR3 comprising the amino acid sequence of SEQ ID NO: 3, and a HCVR CDR3 comprising the amino acid sequence of SEQ ID NO: 6.
or
a) inhibits the invasion and/or growth of *Plasmodium* parasites;
b) has a LCVR CDR2 comprising the amino acid sequence of SEQ ID NO: 2; and
c) has a HCVR CDR3 comprising the amino acid sequence of SEQ ID NO: 6, and
   may further has a LCVR CDR1 comprising the amino acid sequence of SEQ ID NO: 1, and a HCVR CDR2 comprising the amino acid sequence of SEQ ID NO: 5, and/or
   may further has a LCVR CDR3 comprising the amino acid sequence of SEQ ID NO: 3, and a HCVR CDR1 comprising the amino acid sequence of SEQ ID NO: 4.
or
a) inhibits the invasion and/or growth of *Plasmodium* parasites;
b) has a LCVR CDR2 comprising the amino acid sequence of SEQ ID NO: 2; and
c) has a HCVR CDR2 comprising the amino acid sequence of SEQ ID NO: 5, and
   may further has a LCVR CDR1 comprising the amino acid sequence of SEQ ID NO: 1, and a HCVR CDR1 comprising the amino acid sequence of SEQ ID NO: 4, and/or
   may further having a LCVR CDR3 comprising the amino acid sequence of SEQ ID NO: 3, and a HCVR CDR3 comprising the amino acid sequence of SEQ ID NO: 6.
or
a) inhibits the invasion and/or growth of *Plasmodium* parasites;
b) has a LCVR CDR2 comprising the amino acid sequence of SEQ ID NO: 2; and
c) has a HCVR CDR1 comprising the amino acid sequence of SEQ ID NO: 4, and
   may further has a LCVR CDR1 comprising the amino acid sequence of SEQ ID NO: 1, and a HCVR CDR2 comprising the amino acid sequence of SEQ ID NO: 5, and/or
   may further having a LCVR CDR3 comprising the amino acid sequence of SEQ ID NO: 3, and a HCVR CDR3 comprising the amino acid sequence of SEQ ID NO: 6.
or
a) inhibits the invasion and/or growth of *Plasmodium* parasites;
b) has a LCVR CDR3 comprising the amino acid sequence of SEQ ID NO: 3; and
c) has a HCVR CDR2 comprising the amino acid sequence of SEQ ID NO: 5, and
   may further has a LCVR CDR1 comprising the amino acid sequence of SEQ ID NO: 1, and a HCVR CDR1 comprising the amino acid sequence of SEQ ID NO: 4, and/or
   may further has a LCVR CDR2 comprising the amino acid sequence of SEQ ID NO: 2, and a HCVR CDR3 comprising the amino acid sequence of SEQ ID NO: 6.
or
a) inhibits the invasion and/or growth of *Plasmodium* parasites;
b) has a LCVR CDR3 comprising the amino acid sequence of SEQ ID NO: 3; and
c) has a HCVR CDR1 comprising the amino acid sequence of SEQ ID NO: 4, and
   may further has a LCVR CDR2 comprising the amino acid sequence of SEQ ID NO: 2, and a HCVR CDR2 comprising the amino acid sequence of SEQ ID NO: 5, and/or
   may further has a LCVR CDR1 comprising the amino acid sequence of SEQ ID NO: 1, and a HCVR CDR3 comprising the amino acid sequence of SEQ ID NO: 6.

In some embodiments, the isolated human antibody or the antigen-binding portion thereof according to the present disclosure has the following characteristics:
a) inhibits the invasion or growth of *Plasmodium* parasites;
b) has a LCVR CDR1 comprising the amino acid sequence of SEQ ID NO: 16; and
c) has a HCVR CDR3 comprising the amino acid sequence of SEQ ID NO: 6, and
   may further has a LCVR CDR2 comprising the amino acid sequence of SEQ ID NO: 17, and a HCVR CDR2 comprising the amino acid sequence of SEQ ID NO: 5, and/or may further has a LCVR CDR3 comprising the amino acid sequence of SEQ ID NO: 18, and a HCVR CDR1 comprising the amino acid sequence of SEQ ID NO: 4.

or
a) inhibits the invasion and/or growth of *Plasmodium* parasites;
b) has a LCVR CDR1 comprising the amino acid sequence of SEQ ID NO: 16; and
c) has a HCVR CDR2 comprising the amino acid sequence of SEQ ID NO: 5, and
  may further has a LCVR CDR2 comprising the amino acid sequence of SEQ ID NO: 17, and a HCVR CDR1 comprising the amino acid sequence of SEQ ID NO: 4, and/or
  may further has a LCVR CDR3 comprising the amino acid sequence of SEQ ID NO: 18, and a HCVR CDR3 comprising the amino acid sequence of SEQ ID NO: 6.

or
a) inhibits the invasion and/or growth of *Plasmodium* parasites;
b) has a LCVR CDR1 comprising the amino acid sequence of SEQ ID NO: 16; and
c) has a HCVR CDR1 comprising the amino acid sequence of SEQ ID NO: 4, and
  may further has a LCVR CDR2 comprising the amino acid sequence of SEQ ID NO: 17, and a HCVR CDR2 comprising the amino acid sequence of SEQ ID NO: 5, and/or
  may further has a LCVR CDR3 comprising the amino acid sequence of SEQ ID NO: 18, and a HCVR CDR3 comprising the amino acid sequence of SEQ ID NO: 6.

or
a) inhibits the invasion and/or growth of *Plasmodium* parasites;
b) has a LCVR CDR2 comprising the amino acid sequence of SEQ ID NO: 17; and
c) has a HCVR CDR3 comprising the amino acid sequence of SEQ ID NO: 6, and
  may further has a LCVR CDR1 comprising the amino acid sequence of SEQ ID NO: 16, and a HCVR CDR2 comprising the amino acid sequence of SEQ ID NO: 5, and/or
  may further has a LCVR CDR3 comprising the amino acid sequence of SEQ ID NO: 18, and a HCVR CDR1 comprising the amino acid sequence of SEQ ID NO: 4.

or
a) inhibits the invasion and/or growth of *Plasmodium* parasites;
b) has a LCVR CDR2 comprising the amino acid sequence of SEQ ID NO: 17; and
c) has a HCVR CDR2 comprising the amino acid sequence of SEQ ID NO: 5, and
  may further has a LCVR CDR1 comprising the amino acid sequence of SEQ ID NO: 16, and a HCVR CDR1 comprising the amino acid sequence of SEQ ID NO: 4, and/or
  may further having a LCVR CDR3 comprising the amino acid sequence of SEQ ID NO: 18, and a HCVR CDR3 comprising the amino acid sequence of SEQ ID NO: 6.

or
a) inhibits the invasion and/or growth of *Plasmodium* parasites;
b) has a LCVR CDR2 comprising the amino acid sequence of SEQ ID NO: 17; and
c) has a HCVR CDR1 comprising the amino acid sequence of SEQ ID NO: 4, and
  may further has a LCVR CDR1 comprising the amino acid sequence of SEQ ID NO: 16, and a HCVR CDR2 comprising the amino acid sequence of SEQ ID NO: 5, and/or
  may further having a LCVR CDR3 comprising the amino acid sequence of SEQ ID NO: 18, and a HCVR CDR3 comprising the amino acid sequence of SEQ ID NO: 6.

or
a) inhibits the invasion and/or growth of *Plasmodium* parasites;
b) has a LCVR CDR3 comprising the amino acid sequence of SEQ ID NO: 18; and
c) has a HCVR CDR2 comprising the amino acid sequence of SEQ ID NO: 5, and
  may further has a LCVR CDR1 comprising the amino acid sequence of SEQ ID NO: 16, and a HCVR CDR1 comprising the amino acid sequence of SEQ ID NO: 4, and/or
  may further has a LCVR CDR2 comprising the amino acid sequence of SEQ ID NO: 17, and a HCVR CDR3 comprising the amino acid sequence of SEQ ID NO: 6.

or
a) inhibits the invasion and/or growth of *Plasmodium* parasites;
b) has a LCVR CDR3 comprising the amino acid sequence of SEQ ID NO: 18; and
c) has a HCVR CDR1 comprising the amino acid sequence of SEQ ID NO: 4, and
  may further has a LCVR CDR2 comprising the amino acid sequence of SEQ ID NO: 17, and a HCVR CDR2 comprising the amino acid sequence of SEQ ID NO: 5, and/or
  may further has a LCVR CDR1 comprising the amino acid sequence of SEQ ID NO: 16, and a HCVR CDR3 comprising the amino acid sequence of SEQ ID NO: 6.

In an isolated human antibody, or antigen-binding portion thereof, according to the present disclosure the LCVR may comprises the amino acid sequences of SEQ ID NOs 1, 2 and 3 and the HCVR may comprises the amino acid sequences of SEQ ID NOs 4, 5 and 6; or
  a) comprises a heavy chain CDR3 comprising the amino acid sequence of SEQ ID NO: 6, a heavy chain CDR2 comprising the amino acid sequence of SEQ ID NO: 5 and a heavy chain CDR1 comprising the amino acid sequence of SEQ ID NO: 4, or homologous polypeptides or mutants thereof having one or more amino acid substitutions at a contact position or a hypermutation position; and
  b) comprises a light chain CDR3 comprising the amino acid sequence of SEQ ID NO: 3, a light chain CDR2 comprising the amino acid sequence of SEQ ID NO: 2, and a light chain CDR1 comprising the amino acid sequence of SEQ ID NO: 1, or homologous polypeptides or mutants thereof having one or more amino acid substitutions at a contact position or a hypermutation position, or
  may has a light chain variable region (LCVR) comprising the polypeptide of SEQ ID NO: 15 and a heavy chain variable region (HCVR) comprising a polypeptide of SEQ ID NO: 14, or homologous polypeptides thereof, in particular the isolated antibody or the antibody fragment thereof comprises a HCVR/LCVR with an amino acid sequence having at least 80 percent sequence identity, in particular 85% percent sequence identity, to either SEQ ID NO: 15 or 14.

In an isolated human antibody, or antigen-binding portion thereof, according to the present disclosure the LCVR may comprises the amino acid sequences of SEQ ID NOs 16, 17 and 18 and the HCVR may comprises the amino acid sequences of SEQ ID NOs 4, 5 and 6; or a) comprises a heavy chain CDR3 comprising the amino acid sequence of SEQ ID NO: 6, a heavy chain CDR2 comprising the amino acid sequence of SEQ ID NO: 5 and a heavy chain CDR1 comprising the amino acid sequence of SEQ ID NO: 4, or homologous polypeptides or mutants thereof having one or more amino acid substitutions at a contact position or a hypermutation position; and b) comprises a light chain CDR3 comprising the amino acid sequence of SEQ ID NO: 18, a light chain CDR2 comprising the amino acid sequence of SEQ ID NO: 17, and a light chain CDR1 comprising the amino acid sequence of SEQ ID NO: 16, or homologous polypeptides or mutants thereof having one or more amino acid substitutions at a contact position or a hypermutation position, or may has a light chain variable region (LCVR) comprising the polypeptide of SEQ ID NO: 15 and a heavy chain variable region (HCVR) comprising a polypeptide of SEQ ID NO: 14, or homologous polypeptides thereof, in particular the isolated antibody or the antibody fragment thereof comprises a HCVR/LCVR with an amino acid sequence having at least 80 percent sequence identity, in particular 85% percent sequence identity, to either SEQ ID NO: 15 or 14.

The isolated human antibody according to the present disclosure may comprise a heavy chain constant region selected from the group consisting of IgG1, IgG2, IgG3, IgG4, IgM, IgA and IgE constant regions, in particular the antibody heavy chain constant region may be IgG1 or IgG3.

The antigen-binding portion of an isolated human antibody according to the present disclosure may be
 a Fab fragment or a multimer thereof
 a F(ab')2 fragment or a multimer thereof
 a single chain Fv fragment or a multimer thereof.

Furthermore, the present disclosure pertains to:
An isolated nucleic acid molecule, selected from the group consisting of
 a) a nucleic acid molecule encoding the isolated antibody or antigen-binding portion thereof according to the present disclosure;
 b) a nucleic acid molecule encoding for a modified form of the isolated antibody or antigen-binding portion thereof according to the present disclosure, preferably in which one or more amino acid residues are conservatively substituted;
 c) a nucleic acid molecule that is a fraction, variant, homologue, derivative, or fragment of the nucleic acid molecule presented as SEQ ID NO:7, SEQ ID NO:8, SEQ ID NO:9 SEQ ID NO:10 SEQ ID NO:11 or SEQ ID NO:12;
 d) a nucleic acid molecule encoding fragments of the isolated antibody or antigen-binding portion thereof according to the present disclosure
 e) a nucleic acid molecule that is capable of hybridizing to any of the nucleic acid molecules of a)-d) under stringent conditions
 f) a nucleic acid molecule that is capable of hybridizing to the complement of any of the nucleic acid molecules of a)-e) under stringent conditions
 g) a nucleic acid molecule having a sequence identity of at least 85% with any of the nucleic acid molecules of a)-f) and encoding for an antibody or antigen-binding portion thereof,
 h) or a complement of any of the nucleic acid molecules of a)-g).

Furthermore, the present disclosure pertains to:
An isolated nucleic acid molecule, selected from the group consisting of
 a) a nucleic acid molecule encoding the isolated antibody or antigen-binding portion thereof according to the present disclosure;
 b) a nucleic acid molecule encoding for a modified form of the isolated antibody or antigen-binding portion thereof according to the present disclosure, preferably in which one or more amino acid residues are conservatively substituted;
 c) a nucleic acid molecule that is a fraction, variant, homologue, derivative, or fragment of the nucleic acid molecule presented as SEQ ID NO:20, SEQ ID NO:21, SEQ ID NO:22 SEQ ID NO:10 SEQ ID NO:11 or SEQ ID NO:12;
 d) a nucleic acid molecule encoding fragments of the isolated antibody or antigen-binding portion thereof according to the present disclosure
 e) a nucleic acid molecule that is capable of hybridizing to any of the nucleic acid molecules of a)-d) under stringent conditions
 f) a nucleic acid molecule that is capable of hybridizing to the complement of any of the nucleic acid molecules of a)-e) under stringent conditions
 g) a nucleic acid molecule having a sequence identity of at least 85% with any of the nucleic acid molecules of a)-f) and encoding for an antibody or antigen-binding portion thereof,
 h) or a complement of any of the nucleic acid molecules of a)-g).

The isolated nucleic acid molecule may comprise at least two polynucleotides having a sequence selected from the group consisting of SEQ ID NO:7, SEQ ID NO:8, SEQ ID NO:9 SEQ ID NO:10 SEQ ID NO:11 and SEQ ID NO:12 and variants thereof, as permitted by the degeneracy of the genetic code.

The isolated nucleic acid molecule may comprise at least two polynucleotides having a sequence selected from the group consisting of SEQ ID NO:20, SEQ ID NO:21, SEQ ID NO:22 SEQ ID NO:10 SEQ ID NO:11 and SEQ ID NO:12 and variants thereof, as permitted by the degeneracy of the genetic code.

The isolated nucleic acid molecule may comprises polynucleotides with the sequences of SEQ ID NO:7, SEQ ID NO:8, SEQ ID NO:9 SEQ ID NO:10 SEQ ID NO:11 and SEQ ID NO:12 and variants thereof, as permitted by the degeneracy of the genetic code.

The isolated nucleic acid molecule may comprises polynucleotides with the sequences of SEQ ID NO:20, SEQ ID NO:21, SEQ ID NO:22 SEQ ID NO:10 SEQ ID NO:11 and SEQ ID NO:12 and variants thereof, as permitted by the degeneracy of the genetic code.

A vector comprising a nucleotide molecule according to the present disclosure.

A host cell comprising a vector of claim 43.

A composition comprising an antibody or antigen-binding portion thereof according to the present disclosure, wherein the composition is preferably a pharmaceutical and/or diagnostic composition.

A pharmaceutical composition comprising the antibody or an antigen binding portion thereof according to any one of claims 1 to 39 and a pharmaceutically acceptable carrier, wherein The pharmaceutical composition may further comprise an additional agent, in particular a therapeutic agent.

The use of an isolated antibody or antigen-binding portion thereof according to the present disclosure in the prevention and/or treatment of malaria, in particular of malaria tropica.

A purified complex comprising an isolated antibody or antigen-binding portion thereof according to the present disclosure as a specific binding domain and an effector domain, wherein the complex preferably comprises a fusion protein including the binding domain and the effector domain, wherein.

the effector domain may be a toxic substance or a therapeutic agent.

A nucleic acid molecule coding for the complex according to the present disclosure.

A method of producing an isolated antibody or antigen-binding portion thereof according to the present disclosure, wherein the method comprises:
 (a) providing a nucleic acid construct comprising a nucleic acid encoding the antibody or antigen-binding portion thereof,
 (b) introducing the nucleic acid construct into a host cell, and
 (c) maintaining the host cell under conditions permitting expression of the antibody or antigen-binding portion thereof, wherein the host cell may be a plant cell.

the plant may be selected from the group consisting of algae, moss, monocotyledons and/or dicotyledons.

the plant may be selected from a genus from the group consisting of *Apium, Arabidopsis, Brassica, Capsium, Daucus, Hordeum, Lactuca, Lycopersicon, Nicotiana, Petunia, Sinapis, Solanum, Triticum* or *Zea* the plant may be *Nicotiana benthamiana* or *Nicotiana tabacum*.

the antibodies or antigen-binding portions thereof may be isolated and/or purified.

Furthermore, the present disclosure pertains to an isolated human antibody, or antigen-binding portion thereof, that binds to merozoite surface protein 10 (MSP-10) of *Plasmodium* parasites, in particular to MSP-10 of *Plasmodium falciparum*, wherein said antibody or antigen-binding portion thereof inhibits the invasion of a *Plasmodium* parasite into the erythrocyte and/or the growth of the *Plasmodium* parasite within the erythrocyte.

Further embodiments relates to an isolated human antibody, or antigen-binding portion thereof, that binds specific to the first epidermal growth factor-like domain of MSP-10 (SEQ ID NO: 13) of *Plasmodium falciparum*, wherein said antibody or antigen-binding portion thereof inhibits the invasion of a *Plasmodium falciparum* parasite into the erythrocyte and/or the growth of the *Plasmodium falciparum* parasite within the erythrocyte.

The isolated human antibody according to the present disclosure or the antigen-binding portion thereof may have a light chain variable region (LCVR) comprising a polypeptide having a sequence selected from the group consisting of SEQ ID NO: 1, SEQ ID NO: 2 and SEQ ID NO: 3 and a heavy chain variable region (HCVR) comprising a polypeptide having a sequence selected from the group consisting of SEQ ID NO: 4, SEQ ID NO: 5 and SEQ ID NO: 6, or homologous polypeptides thereof.

Furthermore, in the isolated human antibody according to the present disclosure or the antigen-binding portion thereof, the LCVR may comprise the amino acid sequences of SEQ ID NOs 1, 2 and 3 and the HCVR may comprise the amino acid sequences of SEQ ID NOs 4, 5 and 6, or homologous polypeptides thereof.

Further, the disclosed antibody or the antigen-binding portion thereof may have a light chain variable region (LCVR) comprising the polypeptide of SEQ ID NO: 15 and a heavy chain variable region (HCVR) comprising a polypeptide of SEQ ID NO: 14.

The isolated antibody or the antibody fragment thereof may comprise a HCVR/LCVR comprising an amino acid sequence having at least 80 percent sequence identity, in particular at least 85% percent sequence identity, to either SEQ ID NO: 15 or 14.

According to the present disclosure, the antigen-binding portion may be a Fab fragment, a F(ab')2 fragment, a single chain Fv fragment or multimers thereof.

The present disclosure is further directed to an isolated nucleic acid molecule, selected from the group consisting of
 a) a nucleic acid molecule encoding the isolated antibody or antigen-binding portion thereof according to the present disclosure;
 b) a nucleic acid molecule encoding for a modified form of the isolated antibody or antigen-binding portion thereof according to the present disclosure, preferably in which one or more amino acid residues are conservatively substituted;
 c) a nucleic acid molecule that is a fraction, variant, homologue, derivative, or fragment of the nucleic acid molecule presented as SEQ ID NO:7, SEQ ID NO:8, SEQ ID NO:9 SEQ ID NO:10 SEQ ID NO:11 or SEQ ID NO:12;
 d) a nucleic acid molecule encoding fragments of the isolated antibody or antigen-binding portion thereof according to the present disclosure,
 e) a nucleic acid molecule that is capable of hybridizing to any of the nucleic acid molecules of a)-d) under stringent conditions
 f) a nucleic acid molecule that is capable of hybridizing to the complement of any of the nucleic acid molecules of a)-e) under stringent conditions
 g) a nucleic acid molecule having a sequence identity of at least 85% with any of the nucleic acid molecules of a)-f) and encoding for an antibody or antigen-binding portion thereof,
 h) or a complement of any of the nucleic acid molecules of a)-g).

In some advantageous embodiments, the polynucleotide comprises at least two polynucleotides having a sequence selected from the group consisting of SEQ ID NO: 7, SEQ ID NO: 8, SEQ ID NO: 9 SEQ ID NO: 10 SEQ ID NO: 11 and SEQ ID NO: 12 and variants thereof, as permitted by the degeneracy of the genetic code.

Further a vector is disclosed comprising a nucleotide molecule according to the present disclosure and a host cell comprising the vector.

Furthermore, a pharmaceutical composition is disclosed comprising the antibody or an antigen binding portion thereof according to the present disclosure and a pharmaceutically acceptable carrier and the use of the isolated antibody or antigen-binding portion thereof in the prevention and/or treatment of malaria, in particular of malaria tropica.

REFERENCES

The contents of all cited references, including literature references, issued patents, and published patent applications, as cited throughout this application are hereby expressly incorporated by reference.

1. Noedl, H., Socheat, D. & Satimai, W. Artemisinin-resistant malaria in Asia. *The New England journal of medicine* 361, 540-1 (2009).
2. Borrmann, S. et al. Declining responsiveness of *Plasmodium falciparum* infections to artemisinin-based combination treatments on the Kenyan coast. *PloS one* 6, e26005 (2011).
3. Kabat, E. A., Wu, T. T., Gottesman, K. S. & Foeller, C. *Sequences of Proteins of Immunological Interest.* 2719 (DIANE Publishing: 1992).
4. Chothia, C. & Lesk, A. M. Canonical structures for the hypervariable regions of immunoglobulins. *Journal of molecular biology* 196, 901-17 (1987).
5. Chothia, C. et al. Conformations of immunoglobulin hypervariable regions. *Nature* 342, 877-83
6. Marks, J. D. et al. By-passing immunization: building high affinity human antibodies by chain shuffling. *Bio/technology* (Nature Publishing Company) 10, 779-83 (1992).
7. Ward, E. S., Güssow, D., Griffiths, A. D., Jones, P. T. & Winter, G. Binding activities of a repertoire of single immunoglobulin variable domains secreted from *Escherichia coli*. *Nature* 341, 544-6 (1989).
8. Bird, R. E. et al. Single-chain antigen-binding proteins. *Science* (New York, N.Y.) 242, 423-6 (1988).
9. Huston, J. S. et al. Protein engineering of antibody binding sites: recovery of specific activity in an anti-digoxin single-chain Fv analogue produced in *Escherichia coli*. *Proceedings of the National Academy of Sciences of the United States of America* 85, 5879-83 (1988).
10. Holliger, P., Prospero, T. & Winter, G. "Diabodies": small bivalent and bispecific antibody fragments. *Proceedings of the National Academy of Sciences of the United States of America* 90, 6444-8 (1993).
11. Reiter, Y., Brinkmann, U., Lee, B. & Pastan, I. Engineering antibody Fv fragments for cancer detection and therapy: disulfide-stabilized Fv fragments. *Nature biotechnology* 14, 1239-45 (1996).
12. Hu, S. et al. Minibody: A novel engineered anti-carcinoembryonic antigen antibody fragment (single-chain Fv-CH3) which exhibits rapid, high-level targeting of xenografts. *Cancer research* 56, 3055-61 (1996).
13. Poljak, R. J. Production and structure of diabodies. *Structure* (London, England: 1993) 2, 1121-3 (1994).
14. Kipriyanov, S. M., Breitling, F., Little, M. & Dübel, S. Single-chain antibody streptavidin fusions: tetrameric bifunctional scFv-complexes with biotin binding activity and enhanced affinity to antigen. *Human antibodies and hybridomas* 6, 93-101 (1995).
15. Kipriyanov, S. M., Dübel, S., Breitling, F., Kontermann, R. E. & Little, M. Recombinant single-chain Fv fragments carrying C-terminal cysteine residues: production of bivalent and biotinylated miniantibodies. *Molecular immunology* 31, 1047-58 (1994).
16. Taylor, L. D. et al. A transgenic mouse that expresses a diversity of human sequence heavy and light chain immunoglobulins. *Nucleic acids research* 20, 6287-95 (1992).
17. Geysen, H. M., Meloen, R. H. & Barteling, S. J. Use of peptide synthesis to probe viral antigens for epitopes to a resolution of a single amino acid. *Proceedings of the National Academy of Sciences of the United States of America* 81, 3998-4002 (1984).
18. Livingstone, C. D. & Barton, G. J. Protein sequence alignments: a strategy for the hierarchical analysis of residue conservation. *Computer applications in the biosciences: CABIOS* 9, 745-56 (1993).
19. Taylor, W. R. The classification of amino acid conservation. *Journal of theoretical biology* 119, 205-18 (1986).
20. Dayhoff, M. O. *Atlas of Protein Sequence and Structure* (Vol 5, Supplement 3). 353-358 (Natl Biomedical Research: 1979).
21. Smith, T. F. & Waterman, M. S. Comparison of biosequences. *Advances in Applied Mathematics* 2, 482-489 (1981).
22. Altschul, S. F., Gish, W., Miller, W., Myers, E. W. & Lipman, D. J. Basic local alignment search tool. *Journal of molecular biology* 215, 403-10 (1990).
23. Hoogenboom, H. R. & Winter, G. By-passing immunisation. Human antibodies from synthetic repertoires of germline VH gene segments rearranged in vitro. *Journal of molecular biology* 227, 381-8 (1992).
24. Reisfeld, R. A. et al. *Monoclonal antibodies and cancer therapy: proceedings of the Roche-UCLA Symposium held in Park City, Utah*, Jan. 26-Feb. 2, 1985. 609 (A. R. Liss: 1985).
25. Boerner, P., Lafond, R., Lu, W. Z., Brams, P. & Royston, I. Production of antigen-specific human monoclonal antibodies from in vitro-primed human splenocytes. *Journal of immunology* (Baltimore, Md.: 1950) 147, 86-95 (1991).
26. Stöcker, M. et al. Secretion of functional anti-CD30-angiogenin immunotoxins into the supernatant of transfected 293T-cells. *Protein expression and purification* 28, 211-9 (2003).
27. Boes, A. et al. Affinity purification of a framework 1 engineered mouse/human chimeric IgA2 antibody from tobacco. *Biotechnology and bioengineering* 108, 2804-14 (2011).
28. Sambrook, J., Fritsch, E. F. & Maniatis, T. Molecular Cloning: A Laboratory Manual, Volume 1 to 3, 2nd edition. *Sambrook J E F Fritsch and T Maniatis Molecular Cloning A Laboratory Manual Second Edition Vols 1 2 and 3 Cold Spring Harbor Laboratory Press Cold Spring Harbor N.Y. USA Illus Paper* (1989).
29. Ausubel, F. M. et al. Current protocols in molecular biology, edited by M. Ausubel, R. Brent, R. E. Kingston, D. D. Moore, J. G. Seidman, J. A. Smith, and K. Struhl. Volumes 1 and 2. John Wiley & Sons, Inc., Media, PA, 1988, 165.00. *Molecular Reproduction and Development* 1, 146-146 (1989).
30. Boss, M. A., Kenten, J. H., Emtage, J. S. & Wood, C. R. Multichain polypeptides or proteins and processes for their production. (1984).
31. McCafferty, J., Griffiths, A. D., Winter, G. & Chiswell, D. J. Phage antibodies: filamentous phage displaying antibody variable domains. *Nature* 348, 552-4 (1990).
32. Urlaub, G. & Chasin, L. A. Isolation of Chinese hamster cell mutants deficient in dihydrofolate reductase activity. *Proceedings of the National Academy of Sciences of the United States of America* 77, 4216-20 (1980).
33. Kaufman, R. J. & Sharp, P. A. Amplification and expression of sequences cotransfected with a modular dihydrofolate reductase complementary dna gene. *Journal of molecular biology* 159, 601-21 (1982).
34. Fraussen, J. et al. A novel method for making human monoclonal antibodies. *Journal of autoimmunity* 35, 130-4 (2010).
35. Tiller, T. et al. Efficient generation of monoclonal antibodies from single human B cells by single cell RT-PCR and expression vector cloning. *Journal of immunological methods* 329, 112-24 (2008).
36. Brochet, X., Lefranc, M.-P. & Giudicelli, V. IMGT/V-QUEST: the highly customized and integrated system for IG and TR standardized V-J and V-D-J sequence analysis. *Nucleic acids research* 36, W503-8 (2008).
37. Rosenberg, Y. et al. Rapid high-level production of functional HIV broadly neutralizing monoclonal antibodies in transient plant expression systems. *PloS one* 8, e58724 (2013).
38. Roestenberg, M. et al. Safety and immunogenicity of a recombinant *Plasmodium falciparum* AMA1 malaria vaccine adjuvanted with Alhydrogel, Montanide ISA 720 or AS02. *PloS one* 3, e3960 (2008).
39. Kusi, K. A. et al. Immunization with different PfAMA1 alleles in sequence induces clonal imprint humoral responses that are similar to responses induced by the same alleles as a vaccine cocktail in rabbits. *Malaria journal* 10, 40 (2011).
40. Black, C. G., Wang, L., Wu, T. & Coppel, R. L. Apical location of a novel EGF-like domain-containing protein of *Plasmodium falciparum*. *Molecular and biochemical parasitology* 127, 59-68 (2003).
41. Makler, M. T. et al. Parasite lactate dehydrogenase as an assay for *Plasmodium falciparum* drug sensitivity. *The American journal of tropical medicine and hygiene* 48, 739-41 (1993).

The invention claimed is:

1. An isolated monoclonal human antibody, or antigen-binding portion thereof, that binds specific to the first epidermal growth factor-like domain of MSP-10 (SEQ ID NO: 13) of *Plasmodium falciparum*, wherein said antibody or antigen-binding portion thereof inhibits the invasion of a *Plasmodium falciparum* parasite into the erythrocyte and/or the growth of the Plasmodium falciparum parasite within the erythrocyte by at least 50%, wherein the antibody or the antigen-binding portion thereof has a light chain variable region (LCVR) and a heavy chain variable region (HCVR), and wherein the LCVR comprises the CDR sequences of SEQ ID NOs 1, 2 and 3 and the HCVR comprises the CDR sequences of SEQ ID NOs 4, 5 and 6.

2. An isolated monoclonal human antibody, or antigen-binding portion thereof, that binds specific to the first epidermal growth factor-like domain of MSP-10 (SEQ ID NO: 13) of *Plasmodium falciparum*, wherein said antibody or antigen-binding portion thereof inhibits the invasion of a *Plasmodium falciparum* parasite into the erythrocyte and/or the growth of the *Plasmodium falciparum* parasite within the erythrocyte by at least 50%, wherein the antibody or the antigen-binding portion thereof has a light chain variable region (LCVR) and a heavy chain variable region (HCVR), and wherein the LCVR comprises the CDR sequences of SEQ ID NOs 16, 17 and 18 and the HCVR comprises the CDR sequences of SEQ ID NOs 4, 5 and 6.

3. The isolated monoclonal human antibody according to claim 1, wherein the LCVR further comprises the polypeptide of SEQ ID NO: 15 and the HCVR further comprises the polypeptide of SEQ ID NO: 14.

4. The isolated monoclonal human antibody according claim 1, wherein the LCVR further comprises the polypeptide of SEQ ID NO: 19 and the HCVR further comprises the polypeptide of SEQ ID NO: 14.

5. The isolated monoclonal human antibody according to claim 1, wherein the antigen-binding portion is a Fab fragment, a F(ab')2 fragment, a single chain Fv fragment, or multimers thereof.

6. The isolated monoclonal human antibody according to claim 1, comprising a heavy chain constant region selected from the group consisting of IgG1, IgG2, IgG3, IgG4, IgM, IgA and IgE constant regions.

7. The isolated antibody or antigen-binding portion thereof according to claim 1 for use in the treatment of malaria, in particular of malaria tropica.

8. The isolated monoclonal human antibody according to claim 2, wherein the LCVR further comprises the polypeptide of SEQ ID NO: 15 and the further comprises the polypeptide of SEQ ID NO: 14.

9. The isolated monoclonal human antibody according claim 2, wherein the LCVR further comprises the polypeptide of SEQ ID NO: 19 and the HCVR further comprises the polypeptide of SEQ ID NO: 14.

10. The isolated monoclonal human antibody according to claim 2, wherein the antigen-binding portion is a Fab fragment, a F(ab')2 fragment, a single chain Fv fragment, or multimers thereof.

11. The isolated monoclonal human antibody according to claim 2, comprising a heavy chain constant region selected from the group consisting of IgG1, IgG2, IgG3, IgG4, IgM, IgA and IgE constant regions.

12. The isolated antibody or antigen-binding portion thereof according to claim 2 for use in the treatment of malaria, in particular of malaria tropica.

\* \* \* \* \*